(12) United States Patent
Chambers et al.

(10) Patent No.: US 7,327,637 B2
(45) Date of Patent: Feb. 5, 2008

(54) ACOUSTIC PULSE ACTUATOR

(75) Inventors: Joshua M. Chambers, Minneapolis, MN (US); Steven R. Hall, Bedford, MA (US); Jesse M. Simon, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 103 days.

(21) Appl. No.: 11/359,290

(22) Filed: Feb. 22, 2006

(65) Prior Publication Data

US 2006/0236777 A1   Oct. 26, 2006

Related U.S. Application Data

(60) Provisional application No. 60/655,569, filed on Feb. 23, 2005.

(51) Int. Cl.
*H01L 41/00* (2006.01)
*H04R 23/02* (2006.01)
*G01N 29/04* (2006.01)

(52) U.S. Cl. ...................................... 367/140
(58) Field of Classification Search ............... 367/140; 73/801
See application file for complete search history.

(56) References Cited

U.S. PATENT DOCUMENTS

| 4,703,464 | A | 10/1987 | Howarth et al. |
| 5,958,154 | A | 9/1999 | O'Handley et al. |
| 6,779,387 | B2* | 8/2004 | Degertekin ............... 73/105 |
| 6,990,853 | B2* | 1/2006 | Elrod ......................... 73/105 |
| 2003/0041657 | A1* | 3/2003 | Degertekin ............... 73/105 |
| 2003/0041669 | A1* | 3/2003 | Degertekin et al. ....... 73/105 |
| 2004/0118191 | A1* | 6/2004 | Elrod ......................... 73/105 |
| 2006/0075807 | A1* | 4/2006 | Elrod ......................... 73/105 |
| 2006/0236777 | A1* | 10/2006 | Chambers et al. ........ 73/801 |

FOREIGN PATENT DOCUMENTS

| WO | WO 2004/057912 A2 | 7/2004 |
| WO | WO 2006091665 A2 * | 8/2006 |

OTHER PUBLICATIONS

Chambers et al.., "Piezoelectrically induced actuation of NiMnGa ferromagnetic shape memory alloys," SPIE Conf. vol. 5387, Active Materials: Behavior and Mechanics, Abstracts p. 118, Mar. 14, 2004.

(Continued)

*Primary Examiner*—Dan Pihulic
(74) *Attorney, Agent, or Firm*—Theresa A. Lober

(57) ABSTRACT

The invention provides an acoustic actuator, including an acoustic stress wave generator and an actuation material operatively positioned relative to the acoustic stress wave generator for delivery of acoustic stress waves from the generator to the actuation material.

46 Claims, 11 Drawing Sheets

OTHER PUBLICATIONS

Peterson et al., "Acoustic assisted, field-induced strain in ferromagnetic shape memory alloys," Jnl. of Appl. Phys., vol. 95, No. 11, pp. 6963-6964, Jun. 1, 2004.

Marioni et al.., "The ferromagnetic shape-memory effect in Ni-Mn-Ga," Jnl. of Magnetism and Magnetic Materials, vol. 290-291, pp. 35-41, available online Dec. 7, 2004.

Chambers, "Design and Characterization of Acoustic Pulse Shape Memory Alloy Actuators," Thesis, Master of Science in Mechanical Enginnering, MIT, Cambridge, MA, Mar. 4, 2005.

Chambers et al., "Characterization of piezoelectrically induced actuation of Ni-Mn-Ga single crystals," SPIE Conf. vol. 5761, Smart Structures and Materials 2005: Active Materials: Behavior and Mechanics, pp. 478-489, May 2005.

Simon et al., "Transverse acoustic actuation of Ni-Mn-Ga single crystals," SPIE Conf. vol. 6170-61702D, Smart Structures and Materials 2006: Active Materials: Behavior and Mechanics, pp. 61702D-1-61702D-12, Mar. 2006.

* cited by examiner

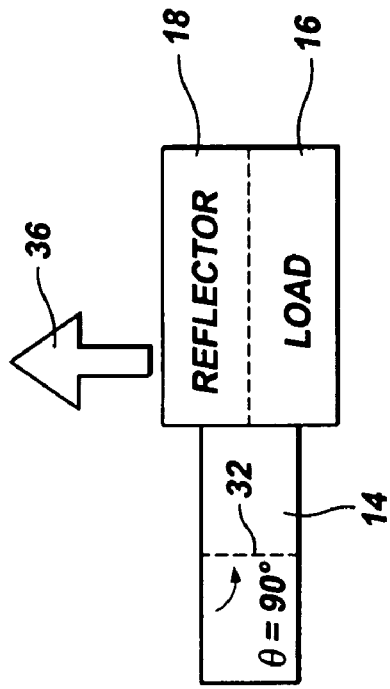
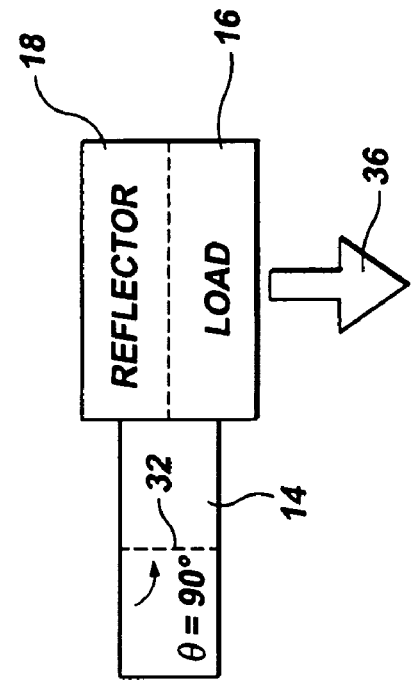
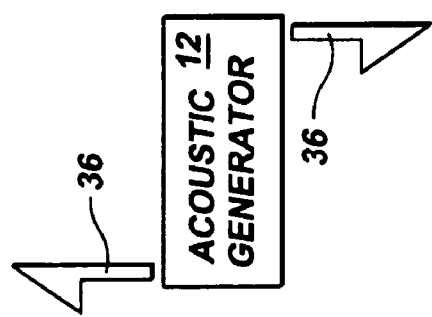
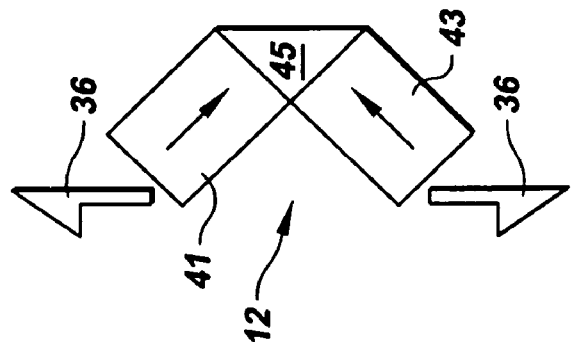
FIG. 3C
FIG. 3D

ACOUSTIC PULSE ACTUATOR

This application claims the benefit of U.S. Provisional Application No. 60/655,569, filed Feb. 23, 2005, the entirety of which is hereby incorporated by reference.

STATEMENT REGARDING FEDERALLY SPONSORED RESEARCH

This invention was made with Government support under Contract No. N0014-01-0758 awarded by Office of Naval Research. The Government has certain rights in the invention.

BACKGROUND OF INVENTION

This invention relates generally to actuators, and more particularly relates to techniques for actuating materials that demonstrate an actuation response to an applied stress.

Many advanced technical applications rely on actuation materials and actuation systems for implementing controlled motion and/or force generation in response to an actuation stimulus such as an applied stress. Popular classes of actuation materials include piezoelectric, magnetostrictive, and thermal and ferromagnetic shape memory alloys. Actuation systems based on these materials exhibit both performance advantages as well as limitations in actuation capabilities.

Piezoelectric materials are characterized by an ability to deform mechanically, i.e., expand and contract, in response to an applied electric field, as a result of the inverse piezoelectric effect. Piezoelectric ceramic actuators, commonly employed in series in the form of a stack, exhibit a very high actuation bandwidth, enabling a fast actuation stroke, while maintaining an acceptable output actuation energy density. Piezoelectric actuators are generally limited, however, to only a relatively small stroke extent, due in part to the brittleness of the piezoelectric ceramic, and in part to the limited strains produced at the maximum practical applied electric field. As a result, a stroke amplification mechanism is often required of a piezoelectric actuation system.

Magnetostrictive actuation materials in general can produce an actuation stroke extent and an actuation force that are greater than those of piezoelectric materials. Application of a magnetic field to a magnetostrictive material causes the material to be strained as the domain magnetization vectors of the material rotate to align with the direction of the applied magnetic field. The unit cells of the material are strained by the magnetization rotation but their orientation is not changed.

Magnetostrictive actuation elements are characterized by a fast actuation response time and by high actuation energy density. But magnetostrictive materials are fundamentally limited by their electrical conductivity, which in general precludes operation at very high actuation frequencies due to the formation of eddy currents in the material in response to a changing applied magnetic field. Like piezoelectric actuation materials, magnetostrictive actuation materials are also characterized by a limited actuation stroke extent, here due to limited domain elongation inherent in the actuation mechanism.

Classical shape memory alloys (SMAs) actuate as they proceed through a diffusionless transformation between a low-temperature, low-symmetry phase known as martensite and a high-temperature, high-symmetry phase known as austenite. In the martensitic phase, portions of the crystal, known as variants, having different crystal structure orientations, often form in pairs, referred to as twin variants. The boundary between twin variants is referred to as a twin boundary. Shifting of twin boundaries allows for low-stress deformation of the low-temperature martensitic phase, and is entirely reversible by returning to the high-temperature austenitic phase. This ability to thermally reverse large stress-induced martensitic deformation results in a large actuation stroke extent. The recoverable strain accommodated by a shape memory alloy is also quite large. Shape memory alloys can be made to act as cyclic or two-way actuators, in a process known as training. In one form of training, the material is cooled below the final martensitic transition temperature, $M_f$, and deformed to take the desired shape. The material is then heated to a temperature above the final austenitic transition temperature, $A_f$, and subsequently allowed to take its austenite shape. The procedure is repeated multiple times, which completes the training. This process programs the material to take one shape when cooled, and another shape when heated.

Thermal control of the martensite-austenite SMA transformation severely limits the actuation response time of classical shape memory alloys, however. As a result, thermal shape memory actuation can not accommodate applications requiring even moderately high actuation frequencies. Thermal control of the shape memory effect also limits the operational temperature range of an actuation system.

Ferromagnetic shape memory alloys (FSMAs) are a subset of shape memory alloys that are characterized by a relatively large magnetocrystalline anisotropy and a low twinning stress in their martensitic phase. In the martensitic phase, twin variants having a magnetization vector that is less favorably oriented with respect to an applied magnetic field physically turn in relation to the field as their magnetization vectors are induced to align with the field. The resulting magnetically-controlled twin boundary motion requires no thermal transformation to the austenitic phase and produces a large actuation stroke extent. Ferromagnetic shape memory alloys are characterized by a moderately fast actuation response and correspondingly high-frequency operation at convenient operating temperatures, typically below 40° C.

The strength of the magnetic field required for ferromagnetic shape memory alloy actuation is in general not trivial to produce, however. Electromagnets designed to produce the required field continuously or with duty cycles greater than a few percent must be substantially larger than the actuation material itself; electromagnets built for continuous actuation must be hundreds of times the volume of a crystal to be actuated. The resulting bulk of a ferromagnetic shape memory alloy actuator prohibits its applicability for many actuation systems.

For many actuation applications, it is ideally preferred to achieve both the large actuation stroke of shape memory alloys and the fast actuation response time of magnetostrictive and piezoelectric materials. At the same time, the thermal constraint of classical shape memory, piezoelectric, and magnetostrictive materials, and the size requirement of ferromagnetic shape memory actuators are also preferably eliminated. Many advanced applications cannot be fulfilled until a single actuation system can address all of these considerations under practical operating conditions.

SUMMARY OF THE INVENTION

The invention overcomes the limitations of conventional actuation systems by providing an acoustically-driven actuator that produces large actuation stroke with fast actuation response time and high output strain, at convenient operating temperatures and with a small form factor. In one example configuration, the acoustic actuator of the invention includes an acoustic stress wave generator and an actuation material operatively positioned relative to the acoustic stress wave generator for delivery of acoustic stress waves from the generator to the actuation material. Superior actuation performance results from a discovery that actuation materials, including those conventionally actuated by, e.g., electric field, magnetic field, and/or temperature field, can instead be actuated by an acoustic stress wave. Thus, the actuation material can in one example be provided as an active material operatively positioned relative to the acoustic stress wave generator to actuate in response to the acoustic stress waves without other actuation stimulus.

The acoustic actuator of the invention is therefore well-suited for a wide range of applications, including, e.g., micropositioning applications. Other features and advantages of the invention will be apparent from the following description and accompanying figures, and from the claims.

DESCRIPTION OF THE DRAWINGS

FIGS. 3B-3D are schematic diagrams of longitudinal acoustic stress wave actuation, and two transverse acoustic stress wave actuation arrangements, respectively;

DETAILED DESCRIPTION OF THE INVENTION

The inventors herein have discovered that a wide range of materials, including materials that can be actuated conventionally, e.g., by electric field, magnetic field, and/or temperature field stimuli, can be actuated by an acoustic stress wave in a manner that overcomes many constraints associated with conventional actuation techniques. The invention provides an actuator configuration for enabling this acoustic actuation technique without the use of conventional actuation stimuli. As explained in detail below, conventional actuation materials, including, e.g., active materials, as well as materials that are not active actuation materials, can be acoustically actuated in accordance with the invention.

Figure 1:
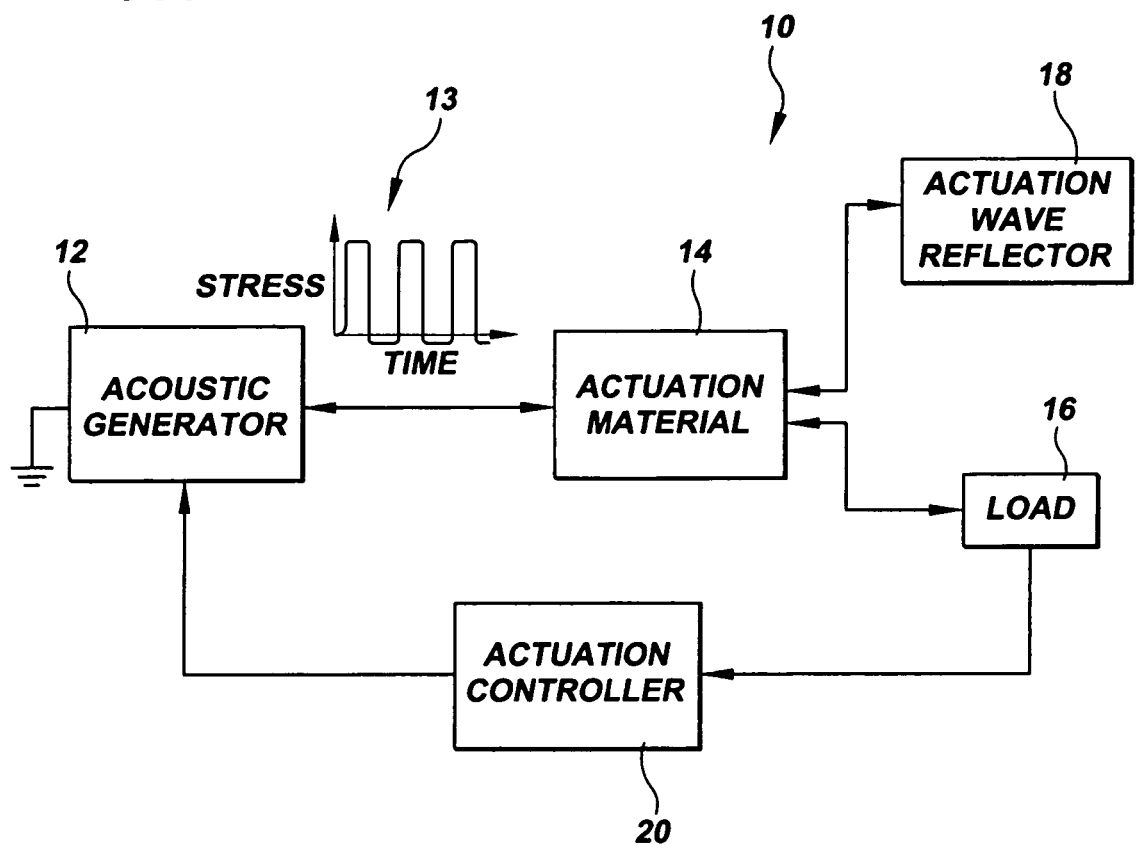
FIG. 1 is a block diagram of an example acoustic actuator provided by the invention.

FIG. 1 is a block diagram of an example acoustic actuation system 10, or acoustic actuator, provided by the invention, for carrying out acoustic actuation of a selected actuation material. The acoustic actuator includes an acoustic generator 12 that produces acoustic stress waves 13 to be imposed on the actuation material 14. The actuation material is coupled or connected to enable mechanical communication with the acoustic generator such that the stress waves are delivered to the actuation material 14. The acoustic generator can be mechanically grounded, as shown in the figure, so that the stress waves are delivered to the actuation material as intended. The transient stress waves 13 then propagate through the actuation material to cause actuation stroke extension or retraction of the material in the manner described in detail below. A load 16 can be provided in mechanical connection with the actuation material for accomplishing work by way of the stroke extension or retraction with the load.

If necessary, as explained below, a stress wave reflector 18 can be provided in mechanical communication with an end of the actuation material opposite that end accepting the stress waves to control reflection of stress waves back through the actuation material. An actuation controller 20 can be provided for controlling the acoustic generator and resulting stroke in actuation material. As explained in detail below, the actuation controller can operate in closed-loop fashion, in the manner shown in FIG. 1, but such is not required; open-loop actuation generation can also be employed.

The schematic acoustic actuator representation in FIG. 1 includes arrows between the various actuator elements to indicate the directionality of mechanical and electrical communication between the elements. For example, the acoustic generator delivers stress waves to the actuation material.

During stroke of the actuation material, mechanical strain and extension or retraction of the material are coupled to the acoustic generator and the wave reflector and load, if included. The position of the load is sensed by the actuation controller for corresponding control of the acoustic generator.

Turning now to each element of the actuator system, the acoustic generator 12 of the actuator can be provided as any mechanism capable of producing acoustic stress waves for actuation of a selected actuation material. The term stress wave herein refers to a wave that propagates through the actuation material acoustically, that is, at roughly the speed of sound in the material, which may be a function of the wave type and its frequency, resulting in transient changes in the stress and strain state of the actuation material. Through controlled mechanical movement or a combination of electrical and mechanical signals and movement, the acoustic generator produces these acoustic stress waves for delivery to a selected actuation material.

The acoustic generator can be a mechanical system, e.g., a striker, a buzzer, or other switch-based mechanism. The acoustic generator can also be provided as, e.g., a rotating cam, or eccentric shaft, in which the eccentricity of the cam causes periodic forces to be applied to the end of the actuation material as the cam displaces or strikes the end of the actuation material. More generally, any mechanical system that can be controlled to periodically strike the end of the actuation material can serve as an acoustic generator in accordance with the invention.

In order to maximize overall energy density of the acoustic actuator system, it can be preferred to employ an acoustic generator that is capable of generating an acoustic stress wave directly, without the need for mechanical amplification. But if necessary, amplification of the output of the acoustic generator can be employed. For example, if an active material, such as a piezoelectric ceramic, is used as the acoustic generator, and is not capable of producing sufficiently large stress levels, then an acoustic horn can be placed between the piezoelectric material and the actuation material. If the horn is tapered, with the smaller end near the actuation material, the horn will amplify the acoustic stress wave, resulting in greater stress levels in the actuation material than without the horn.

For many applications, an active material, such as a piezoelectric, electrostrictive, or magnetostrictive material, is particularly well-suited as an acoustic generator. By active material, herein is meant any material for which the stress or strain state of the material can be changed by the application of a suitable field, including, but not limited to, an electric field, a magnetic field, or a temperature field. Active materials, especially those that are electrically driven, with either electric or magnetic fields, are particularly well suited for use as an acoustic generator. Electrical actuation allows the acoustic generator to be controlled easily by electrical or electronic control systems. Further, active materials allow the profile of the acoustic stress wave to be precisely controlled. Active materials are also attractive because they can be coupled well to the actuation material through the use of conventional bonding techniques. Finally, when the acoustic generator is provided as an active material, the resulting acoustic actuator of the invention is essentially a solid state device, with no assemblies of moving parts, and with little or no mechanical wear; the only movement in the actuator is in this configuration the displacement of the acoustic generator material and the displacement of the actuation material.

Piezoelectric and magnetostrictive materials are capable of generating stresses higher than about 1 MPa and therefore can reliably produce actuation stress magnitudes that are suitable for a range of actuation materials, as described below. It is recognized, however, that magnetostrictive-based devices are limited to significantly lower operating frequencies than piezoelectric-based devices, due to the inductive load of electromagnets required for magnetostriction and the formation of eddy currents during magnetic actuation. Where such issues are not a concern, a magnetostrictive material can be employed for acoustic stress wave generation. One suitable example magnetostrictive material is Terfenol-D, an alloy of terbium, dysprosium, and iron. An example chemical composition of this alloy that can be employed as an acoustic generator material is $Tb_{0.3}Dy_{0.7}Fe_2$.

But in general, the acoustic generator for many applications is preferably electric field-based, rather than magnetic field-based, to accommodate high actuation speeds. Because electric field-based devices can be operated at higher frequencies relative to magnetic field-based devices, electric field-based devices can generate actuation stresses with smaller displacements, and therefore can enable an acoustic generator length shorter than that of magnetic field-based devices.

Considering particular electric field-based acoustic generation materials, electrostrictive materials are also suitable for use as an acoustic generator. Like piezoelectric materials, electrostrictive materials respond to an applied field. Whereas piezoelectric materials respond nearly linearly to the applied field, due to their nearly fixed polarization, electrostrictive materials have a nonlinear, nearly quadratic response, because the applied field both induces a polarization, and then acts on that polarization to produce a material stress or strain. An example electrostrictive ceramic that can be employed as an acoustic generation material is lead-magnesium-niobate (PMN).

For many applications, where an active, electric field-based material is preferred for generation of acoustic stress wave pulses, a piezoelectric-based acoustic actuator is particularly well-suited in accordance with the invention. When an electric field is applied across a piezoelectric material, the material expands or contracts, producing a corresponding acoustic stress wave associated with the mechanical expansion or contraction. This expansion or contraction can be exploited in a range of piezoelectric material configurations in accordance with the invention.

For example, a single-layer piezoelectric device has the advantage of being small, stiff, characterized by a small capacitive load, inexpensive, and elegantly simple in configuration. But for many applications, it is found that a single-layer piezoelectric device is characterized by a mechanical stroke expansion or contraction that is too small to generate a reasonable acoustic stress wave magnitude under practical conditions. Where a suitable acoustic stress wave can be produced by a single-layer piezoelectric device, such can be employed in accordance with the invention. For example, an acoustic generator can be fabricated from a single layer of piezoelectric ceramic sheet with electrodes, e.g., in a configuration such as T180-A4E-602, from Piezo Systems, Inc., of Cambridge, Mass., if such can be configured to produce an acoustic stress wave that is sufficient for actuation.

For many applications, it can therefore be preferred to employ a piezoelectric stack actuator configuration for generating acoustic stress waves. A piezoelectric stack consists of layers of piezoelectric material separated by electrodes provided for generating an electric field across each layer. Application of a voltage across each layer, and across the stack, results in an extension or retraction of the entire stack of piezoelectric layers.

With this configuration, a piezoelectric stack in general produces large displacement, enabling the generation of acoustic stress waves at relatively low voltages. A piezoelectric stack requires high electrical current, however, due to the inherently large capacitance of the layered stack structure. One example piezoelectric stack that can be employed is a Piezo Systems TS18-H5-104 stack, which is a low-voltage (up to 100 V) stack composed of many layers of thin piezoelectric sheets bonded together, with the electrodes to each sheet connected electrically in parallel. The sheets are actuated in 33-mode, meaning that the electric field is applied through the thickness of each sheet, and causes an increase in thickness, so that the net effect is a stack that elongates when a voltage is applied to the stack. The dimensions of this example stack are about 5 mm×5 mm×18 mm.

Where a piezoelectric stack is employed, the large internal stresses that the stack can generate during expansion and contraction make it preferable to mechanically pre-stress a stack acoustic wave generator. Without such a pre-stress condition, a stress wave, generated by the stack itself, that puts the stack in tension, could cause brittle failure of the piezoelectric material layers in the stack. A pre-stress condition also improves the piezoelectric performance by shifting the equilibrium polarization of the piezoelectric material layers. Finally, a pre-stress condition allows the generation of a tensile stress wave by actuation of the stack.

In addition, because a negative voltage applied to the stack could result in depolarization, it is preferred that only positive voltages be employed for expanding or contracting the stack to produce acoustic stress waves. A compressive mechanical pre-stress acts like a negative voltage bias, shifting the operating range of the piezoelectric stack, thereby making an applied positive voltage more effective in acoustic stress wave generation. In one example, using, e.g., a Lead Zirconate Titanate (PZT) piezoelectric stack, a pre-stress of about 6.5 KSI, or 45 MPa is effective for this purpose. In pre-stressing a piezoelectric stack, if a mechanical clamp is to be employed, ideally the clamp would be characterized by zero stiffness. Because such is not realizable as a practical matter, it is preferred to minimize the clamp stiffness relative to that of the piezoelectric stack.

Where an active material, such as a piezoelectric stack configuration, is employed as the acoustic generator, it can be convenient and preferred to directly mount the output end of acoustic generator material to a face of the actuation material, i.e., to directly mechanically couple the stroke output of the active material to the actuation material; an example of this configuration is described in detail below. This direct mechanical connection enables direct transmission of acoustic stress waves, resulting from active material expansion or contraction, from the acoustic generator material to the actuation material, and thereby enhances the efficiency of the actuator.

For this direct mounting configuration, the connections between the acoustic generator and the actuation material, as well as connections between the actuation material and a reflector and load, if included, preferably do not separate during normal operation of the acoustic actuator. Further, the connections between the various materials preferably efficiently transmit the actuating stress wave pulse from the acoustic generator to the actuation material and into the reflector and load. For many actuation materials, such as shape memory actuation materials (SMA), metal-metal bonds are inadequate, due to the sensitivity of SMA actuation properties to changes in composition and heat treatment. Therefore, a polymer adhesive that is not of the heat curing variety can be preferred for bonding acoustic generator, actuation, reflector, and load materials.

The thickness of material bonds between the various actuator materials is also preferably considered for its potential impact on the transmission of acoustic stress wave pulses. Bond lines thicker than about 50 μm can have a detrimental affect on acoustic stress wave propagation. But it is to be recognized that the effect of a bond line on wave propagation can depend on many factors in addition to bond line thickness, including bond material properties and frequency of the stress wave.

It also can be important for some applications to enable electrical coupling through bond lines, e.g., by providing surface roughness of mating surfaces, for making electrical connection to the acoustic actuator. When longitudinal acoustic actuation is to be conducted, as described below, it can be preferred to bond the acoustic generator material to the actuation material with a low-viscosity adhesive, such as cyanoacrylate. A low viscosity adhesive such as this forms a thin bond line that performs well in compression and tension. When transverse actuation is to be conducted, as described below, it can be preferred to bond the acoustic generator material to the actuation material with a high-viscosity adhesive, such as an epoxy adhesive. A high-viscosity adhesive can here be preferred, because it forms a bond line that can accommodate a shear stress without failing.

Considering now the other elements of the acoustic actuator, the actuation material 14 of the acoustic actuator is in general any solid state material that can support propagation of stress waves through the material in a manner that results in a change in material phase or that results in development of strain in the material and/or extension or retraction of the material. As explained above, the inventors herein have discovered that a wide range of materials can be actuated by an acoustic stress wave. This includes active materials that are conventionally actuated by, e.g., electric field, magnetic field, and/or temperature field, and that instead can be actuated by an acoustic stress wave. But the invention is not limited to active materials; as just stated, all that is required of the actuation material is an ability to support propagation of stress waves through the material in a manner that results in a change in material phase or that results in development of strain in the material and/or extension or retraction of the material. This is the case for materials that deform non-elastically. The material deformation can be plastic in that the deformation need not be perfectly reversible, but for many applications, reversible deformation is preferred. This characteristic of reversible deformation is generally achieved by bistable or polystable materials, i.e., materials that exhibit two or more stable mechanical states. The material need not be single crystalline, and can be polycrystalline or include amorphous regions.

Materials characterized by twin variant bistable states are particularly well-suited for acoustic actuation in accordance with the invention, due to their particular actuation mechanism and the ability to invoke that mechanism by an acoustic stress wave. Certain materials, such as some body-centered cubic metals, exhibit a plastic deformation mechanism, known as twinning, in which the crystal structure in regions of the deforming material changes in such a way as to produce a mirror image of the original, undeformed crystal structure.

Figure 2A:
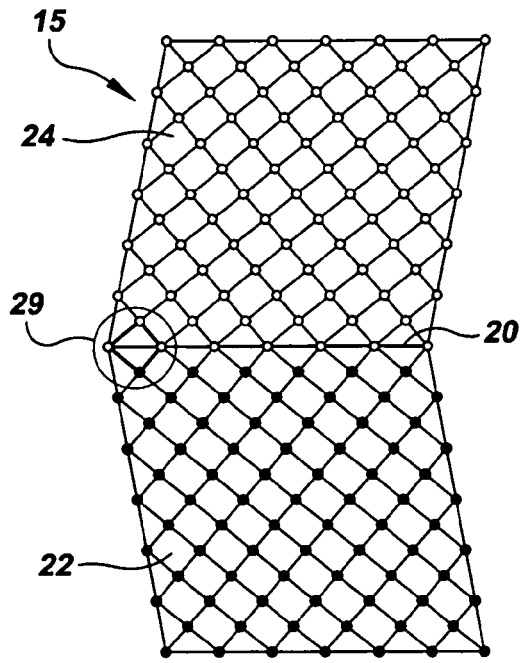
FIGS. 2A-2C are schematic diagrams of a shear stress applied to a twinning material and the resulting crystal reorientation.
Figure 2B:
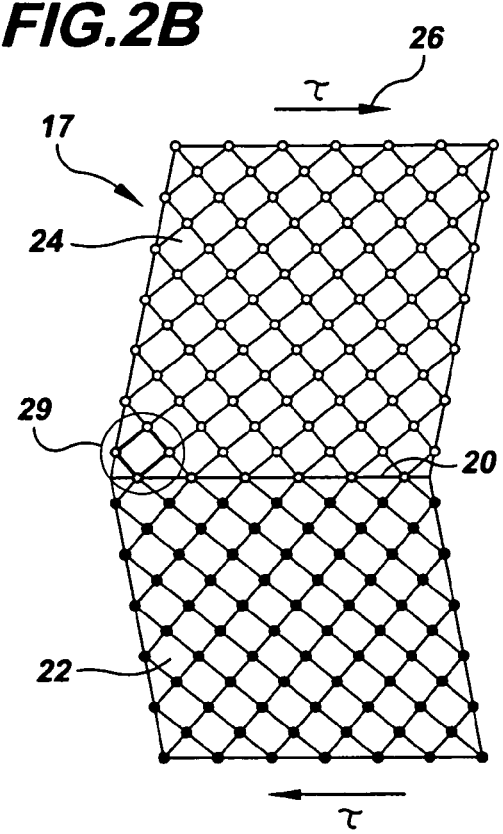

FIGS. 2A-2B are schematic representations of such a twinning material before deformation 15 and a twinning material after deformation 17, respectively. The plane across which the crystal structure is mirrored is known as the twin boundary 20, and the material regions on either side of the twin boundary are known as the twin variants; in FIGS. 2A-2B two twin variants, Variant A 22 and Variant B 24, are shown. Each twin variant represents one stable state of the bistable crystalline structure. Along the twin boundary 20, the unit cells are neither Variant A 22 nor Variant B 24. A single such unit cell 29 is highlighted in FIG. 2A in the twinning material before deformation 15. Unlike the cells in the interior of Variant A 22 and Variant B 24, this cell 29 is not rectangular, but is instead an irregular quadrilateral.

When a shear stress, $\tau$, 26 is applied to the material in the direction shown in FIG. 2B, the atoms of unit cells in the material in the Variant A 22 are induced to reorient to the configuration of atoms in the unit cells of Variant B 24. As this reorientation is initiated, atoms in the Variant A that are located immediately below the twin boundary 20 are able to respond to the shear stress by moving to a position to the left that transforms the irregular unit cells along the twin boundary into rectangular cells of Variant B 24. This has the effect of moving the twin boundary 10 down one layer of atoms. If the shear stress 26 is continuously applied, this process will repeat, causing the twin boundary 20 to move down through the twinning material 17, until the entire crystal is oriented in Variant B 24.

Figure 2C:
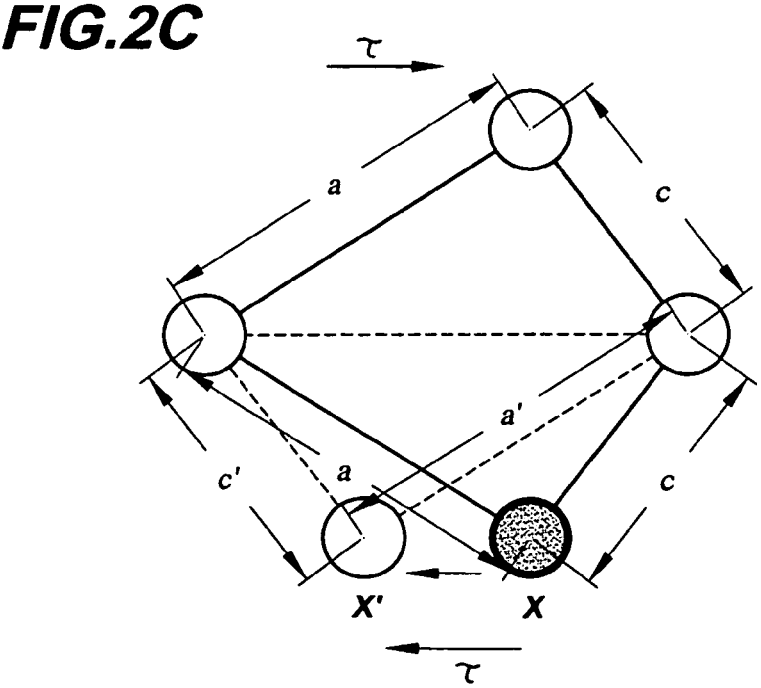

FIG. 2C shows a magnified view of the unit cell 29 during this reorientation. The lengths of the two crystallographic axes of the unit cell 29 are given by a and c, where a>c. As the shear stress 26 causes unit cells of Variant A reorient and the twin boundary passes downward through a cell 29, the atom that was originally at position x moves to a new position x'. This movement results in a new long a axis, here termed a', that lies opposite the original c axis. The macroscopic effect of this shift is the generation of a shear strain as the material reorients from Variant A 22 to Variant B 24. Measured as an engineering shear strain, the magnitude of the shear strain is approximately $\gamma = 2(a-c)/a$.

In practice, most materials that are capable of twinning are characterized by a twinning stress, i.e., the stress necessary to move a twin boundary, that exceeds the plastic yield strength of the material. As a result, most such materials do not tend to deform by twinning unless they are at a very low temperature. For materials that do deform by twinning at reasonable applied stresses not exceeding the yield strength of the material, an acoustic stress wave produced by the acoustic wave generator of the invention can be directed to cause twin variant reorientation and corresponding material extension or retraction by increase and decrease of one or more twin variants.

So long as the stress wave includes a component of shear stress 26, that is oriented along a twin boundary, as shown in FIG. 2B, and that is larger than the twinning stress, the atoms near the twin boundary can move from lattice positions of the first variant to lattice positions of the second variant as the stress wave propagates through the material across the twin boundary. As atoms along the twin boundary plane move into new positions, the twin plane moves in the manner described just above, increasing the extent of one variant and decreasing that of the other. The resulting twinning mechanism of deformation results in a stroke extension or retraction of the actuation material.

The class of materials that deform by twinning and for which the characteristic twinning stress can be overcome by a propagating acoustic stress wave, generated under practical conditions, can be employed as an actuation material in accordance with the invention. It is also preferred that the selected actuation material accommodate hysteretic twinning deformation actuation that is reversible with an opposing acoustic stress wave. This enables both acoustically-actuated stroke extension as well as stroke retraction.

The class of shape memory alloys, including classical, thermally-actuated shape memory alloys and ferromagnetic shape memory alloys, are for many applications the preferred class of actuation material. Many shape memory alloy materials are characterized by a twinning stress that is much lower than the plastic yield strength of the material at room temperature. For such materials, twinning is the dominant deformation mechanism.

One preferred material is the ferromagnetic shape memory alloy Ni—Mn—Ga, particularly in a compositional range of $Ni_xMn_{1.16-1.75x}Ga_{0.75x-0.16}$, where x is between about 0.46 and about 0.52. Ni—Mn—Ga compositions in this range result in a martensitic phase that is either tetragonal or orthorhombic, and both of which are characterized by relatively low twinning stresses. Compositions with lower fractions of manganese, below 30 atomic percent, are generally tetragonal, whereas compositions with greater fraction of manganese are generally orthorhombic. The orthorhombic compositions potentially have greater strain capability, due to the larger ratio between the maximum and minimum lengths of the unit cell edges. However, the tetragonal compositions generally have lower twinning stresses, and it has been found in accordance with the invention that it can be easier to produce working actuation materials with these compositions. The most preferred composition in accordance with the invention is $Ni_{0.52}Mn_{0.22}Ga_{0.26}$. For this case, the crystal lattice cell 29 of FIGS. 2A-2C is characterized by lengths where $c/a = 0.94$, resulting in a developed engineering shear strain of about 12%, following the expression for twinning shear strain given above.

In order for a crystal of Ni—Mn—Ga to operate as an actuation material, the crystal is first suitably prepared, to ensure that the twin planes of the material are properly oriented and that the crystal has a sufficiently low twinning stress for a given actuation application. In one example crystal preparation technique in accordance with the invention, first a crystal of appropriate size is cut, e.g., by Electron Discharge Milling (EDM), from a single crystal boule, such that a potential twin plane is oriented correctly, depending on the mode of actuation desired. For example, for transverse actuation, one of the {202} planes should be perpendicular to the long axis of the crystal, while for longitudinal actuation the long axis should be normal to a {100} plane. The faces are then polished mechanically and the crystal wrapped in, e.g., molybdenum wire. The crystal is then encapsulated in a quartz tube for heat treatment. The molybdenum wire prevents the crystal from making contact with the tube surface, which could allow the formation of manganese silicates. A tantalum getter can also be inserted in the tube to react preferentially with any oxygen that remains in the tube. The tubes is then evacuated and filled with an inert gas, such as argon. The encapsulated crystal is then placed in a furnace. The furnace temperature is increased to a maximum annealing temperature of, e.g., between about 750-900° C., and this temperature is maintained for, e.g., 24 hours. The temperature is then reduced to, e.g., about 500° C. and held constant for about 4 hours. Then the crystal is cooled to, e.g., about 200° C. and held at this temperature until being removed from the furnace.

During a next step of cooling to room temperature, a biasing stress is applied that tends to favor the nucleation of twin boundaries which are correctly oriented for a given mode of actuation. Since there are three potential c-axis orientations as the material cools from the cubic austenitic to the tetragonal martensitic phase, possible {202} planes are (202), (220), and (022). An appropriate biasing stress will tend to form twin boundaries with their normal vectors in only one of these directions. For longitudinal mode crystals, this can be achieved by applying a large compressive stress of up to −10 MPa to the end faces of the crystal, while for transverse mode crystals, magnetic training may be more effective. Here, a shear stress is generated by the application of a magnetic torque. Since in Ni—Mn—Ga alloys the c-axis is most easily magnetized, an unconstrained crystal will tend to rotate so that its c-axis lies parallel to the magnetic field. Thus, restraining the crystal from rotation during the application a magnetic torque results in a shear stress tangent to a twin plane, which has the same effect as the above mechanical training method. Finally it is noted that repeated cycling of the cooled material through its two actuation variants tends to improve twin boundary mobility and thus actuation speed. With this training process complete, the SMA material can be employed as the actuation material in the acoustic actuator of the invention.

Further in consideration of actuation material selection, it is to be recognized that in the case of a conventional, quasi-static actuator, the shear strain generated in an active material such as a piezoelectric ceramic may be multiplied by a linear, mechanical amplification system. The simplest such example would be a lever, in which a small displacement is transformed to a larger one, with a concomitant increase in the force any resistive load places on the material. In contrast, in the acoustic actuator of the invention, it is a stress wave generated by the acoustic stress wave generator that produces a stress in the actuation material. For shape memory actuation materials such as Ni—Mn—Ga alloys, a large strain, e.g., 6% strain, can be achieved as a result, due to the twinning behavior of this actuation material.

Given that the acoustic stress wave generator can be provided as an actuation material itself, such as the piezoelectric stack described above, then one important criterion for selecting the acoustic stress wave generation material and the actuation material to be acoustically actuated is the difference in acoustic impedance between the acoustic stress wave generation material and the acoustically actuated material.

For example, in order for a piezoelectric material to generate acoustic stress waves efficiently in an actuation material, the piezoelectric material should have a higher impedance than actuation material. That is, the impedance of the acoustic generator material, $$Z_{AG} = \sqrt{\rho_{AG} E_{AG}},$$

should be higher, if possible, than the impedance of the actuation material, defined as $$Z = \sqrt{\rho E}.$$

Therefore, it is desirable that the acoustic generator material be both stiffer and denser than the actuation material. As one example, piezoelectric ceramics such as Lead Zirconate Titanate (PZT) are good choices for acoustic generator material, since they are both dense and stiff.

With this specification for the acoustic generator material and for actuation material, further characteristics of the acoustic stress wave can be specified to enable material actuation. It is known that for a longitudinal wave in a thin, prismatic bar of constant cross-section, the differential equation describing the propagation of the stress wave can be expressed as:

$$\rho \frac{\partial^2 u(x,t)}{\partial t^2} - E \frac{\partial^2 u(x,t)}{\partial t^2} = 0, \qquad (1)$$

where u(x, t) is the longitudinal displacement of the bar as a function of longitudinal position, x, along the bar and time, t, ρ is the material density, and E is the Young's modulus of the material. The stress at any location in the bar is given by $$\sigma(x,t) = E \frac{\partial u(x,t)}{\partial x}.$$

Suppose the location x=0 is the end of the actuation material that is in mechanical communication with the acoustic generator. The boundary condition at that end of the bar is $$\frac{\partial u(0,t)}{\partial t} = v_{end}(t),$$

where $v_{end}(t)$ is the velocity of the end of the bar. By controlling the velocity of the end of the bar, the acoustic generator can induce a stress wave, σ(x,t), in the actuation material, which in turn causes twin plane motion, if the magnitude of the stress wave is sufficiently high. For a wave traveling in the +x direction only, the differential equation of Expression (1) above can be solved in closed form, and the resulting normal stress, σ(x, t), imposed by the stress wave on the material then specified as:

$$\sigma(x,t) = -\sqrt{\rho E}\, v_{end}(t - x/c_0), \qquad (2)$$

where $c_0$ is the acoustic stress wave speed, given as $$c_0 = \sqrt{E/\rho}.$$

That is, application of a prescribed velocity at one end of the actuation material by the acoustic generator produces a stress wave that travels at a characteristic speed through the actuation material, and which has magnitude proportional to the applied velocity. The constant of proportionality is $$Z = \sqrt{\rho E},$$

the acoustic impedance.

Thus, the generation of an acoustic stress wave depends critically on the velocity imposed at one end of the actuation material by the acoustic generator. Note that the Expression (2) above is valid only until the stress wave reaches the other end of the actuation material, at which point stress wave reflections must be considered, as discussed below. Nevertheless, the role of applied velocity in producing the acoustic stress wave at the wave generation end of the actuation material is clear from this Expression (2). This analysis can be extended to other types of wave motion, e.g., transverse stress wave propagation, in a straightforward manner, recognizing that the details of the expressions will be different but the form substantially unchanged.

In general, the stress wave is a shaped transient stress wave, characterized by a stress that is sufficient to overcome the internal material stress associated with a particular bistable mechanical state, here termed the actuation stress. With this condition met, the stress wave provides sufficient energy to reorient the actuation material as the wave propagates through the material, resulting in a stroke extension or retraction. For example, given an actuation material that is characterized by twin variants, as explained above, if the stress wave produces a shear stress that is greater than the twin boundary stress, $\sigma_0$, then the stress wave provides sufficient energy to reorient a twin variant associated with the material twin boundaries in the manner described above. Specifically, to enable acoustic actuation, the peak of the stress wave is characterized by a shear stress, resolved along a twin boundary, that is greater than the twinning stress of the actuation material.

It is recognized that as the stress wave propagates through the material, the wave loses energy as it reorients the actuation material from one stable state to another. For example, the stress wave loses energy as twins in a twinning material are reoriented, due to the twinning stiffness. In general, the stress wave also loses strength due to imperfections in the material that lead to dispersion of the stress wave. The stress wave therefore preferably is characterized by a level that is sufficient for reorienting the full extent of the material given the particular characteristics of the material. Thus, the peak magnitude of the stress wave preferably initially exceeds the actuation stress by a margin sufficient for the particular material characteristics of a given actuator implementation.

The actuating stress wave is further specified as an asymmetric waveform. When the actuation material is to be retracted, the asymmetric condition is preferred such that the portion of the stress wave duty cycle that produces a longitudinal compressive stress is greater than the stress required for compressive reorientation of the actuation material, and the portion of the stress wave duty cycle that produces a longitudinal tensile stress is much less than the stress required for tensile reorientation of the actuation material. Similarly, when the actuation material is to be extended, it is preferable that the longitudinal tensile stress generated by a portion of the stress wave duty cycle be greater than the stress required for tensile reorientation of the actuation material, and the portion of the stress wave duty cycle causing a longitudinal compressive stress be much less than the stress required for material compression, or stroke retraction.

For the case of twinning materials, this corresponds to a resolved shear stress greater than the twinning stress, $\sigma_0$, in the desired shearing direction, and a resolved shear stress much less than $\sigma_0$ in the direction opposite the desired shearing direction. Without this condition, the actuation material would both extend and retract with each acoustic stress wave, resulting in a net zero material actuation. Hence, in accordance with the invention, it is not sufficient to use a symmetric stress wave, such as a sinusoidal wave or symmetric square wave, for acoustic actuation; an asymmetric wave is required for most applications. Further, because twin boundary motion is triggered by a threshold twinning stress, it is required only to meet the threshold actuation stress, and no benefit is achieved by significantly exceeding the threshold. To conserve energy, the acoustic stress wave need not be of extreme stress levels.

If the magnitude of the stress wave exceeds that of the material's actuation stress, a material reorientation will occur, e.g., a twin boundary will move at a characteristic velocity corresponding to the actuation material being used. In a theoretical, perfect crystal, there is no resistance to twin boundary motion, and the entire crystal reorients when the magnitude of the stress wave exceeds the twinning stress. In practice, scattering and dispersion of the stress wave in the material, due to twinning stiffness, as well as material defects, result in a finite twin boundary velocity. For the FSMA material Ni—Mn—Ga, this velocity is estimated to be about 10 $ms^{-1}$.

Based on these material considerations, it is found in accordance with the invention that to achieve a desired stress wave magnitude and asymmetry, it can be most important, for many applications, to control how the acoustic generator interacts with the actuation material. Based on Expression (2) and the discussion above, this control is employed to effect a velocity waveform at the end of the actuation material that is large enough to produce a stress wave pulse with magnitude that exceeds the actuation stress of the actuation material in the desired direction, and small enough that the actuation stress magnitude is not exceeded in the opposite direction. In practice, this means that the end velocity generated by the acoustic generator is, e.g., an asymmetric square wave, like that shown in FIG. 1, with a large velocity for a short period of time in one direction, and a small velocity for a longer period of time in the opposite direction. For example, to retract the actuation material, a large velocity toward the actuation material is desired, which produces a large compressive stress, while the return velocity away from the actuation material is smaller, and so produces a smaller tensile stress.

For an acoustic generator comprising an active material such as piezoelectric ceramic stack, the displacement of the acoustic generator is roughly proportional to the voltage applied to the stack. Hence, in the example case of retraction of the actuation material, the profile of the voltage signal applied to the piezoelectric stack is ideally an asymmetric saw-tooth, with a rapid rise time for the saw-tooth, to produce a large positive end velocity and therefore large compressive stress, and a slower fall time, to produce a smaller negative velocity and tensile stress.

Whatever voltage signal is employed to produce the acoustic stress wave, as the acoustic stress wave propagates through the actuation material from a front end of the material, the wave eventually arrives at the back end of the material. If this back end of the actuation material is maintained mechanically free, then a stress-free boundary condition is set up at that back end. Under this condition, when a stress wave arrives at the actuation material back end, there must be reflected from the back end a reflected stress wave of equal and opposite magnitude to that of the original stress wave. The reflected stress wave originates at the material back end and propagates in a direction opposite that of the original stress wave. A tensile stress wave would be reflected as a compressive stress wave, and a compressive stress wave would be reflected as a tensile stress wave. The equal and opposite reflected stress wave reverses the shear strain generated by the incident stress wave, and has the potential to undo the work done by the original actuating stress wave.

This condition can be mitigated by including with the actuation material an actuation wave reflector 18 shown schematically in FIG. 1. The wave reflector is positioned, as shown in FIG. 1, at an end of the actuation material opposite the acoustic generator. It is recognized that even with a reflector in place on the actuation material, a stress wave is still reflected from the end of the reflector material. Thus, the reflector preferably is characterized by geometric and material properties that enhance the tendency of the reflector to disperse the reflected stress wave. Such can be achieved, e.g., by employing a reflector material that has a higher acoustic impedance than the actuation material and/or a cross-section that is different from that of the action material.

If the reflector material is characterized by a higher impedance than the impedance of the actuation material, then the reflected stress wave traveling back from the free end of the reflector will be of the same sign as the initial stress wave. Further, if the reflector is designed appropriately, the magnitude of the reflected wave will be smaller, and hence not unduly detrimental. Thus, it can be preferred for some applications to design the geometry of the reflector to maximize dispersion of the reflected stress wave before the reflected stress wave arrives back at the actuation material. Specifically, the reflector is preferably provided with a minimum length that is sufficient for significantly suppressing a reflected stress wave in the actuation material by scattering the wave in the reflector material. This minimum length is determined by noting that for a reflector to have a significant scattering effect on a stress wave of wavelength $\lambda$, the minimum reflector length should be a significant fraction of $\lambda$, e.g., $\lambda/4$. Mechanical simulation can be undertaken to design a reflector, e.g., a reflector horn geometry, that also maximizes stress wave dispersion. It is found for many applications, however, that a simple block reflector can be adequate. For example, a simple block of, e.g., brass, having dimensions slightly larger than the cross-section of the actuation material, is adequate for most applications.

Figure 3A:
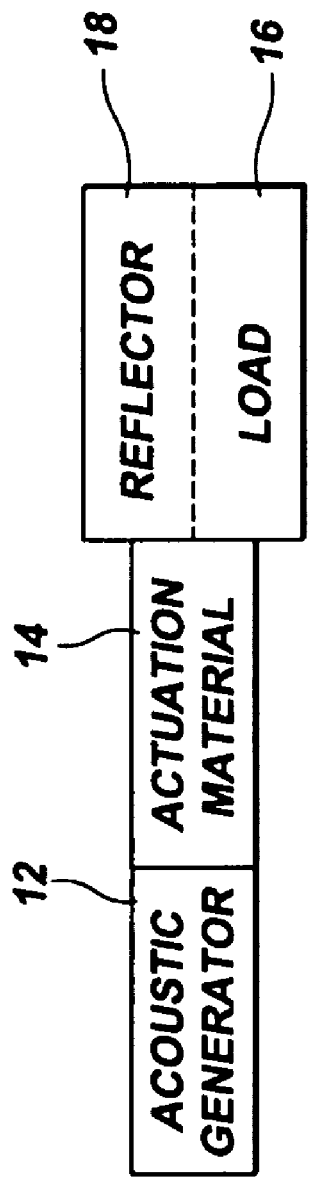
FIG. 3A is a schematic diagrams of an example configuration of an acoustic generator and an actuation material in accordance with the invention.

Referring now to FIG. 3A, considering the macroscopic arrangement of the acoustic actuator elements, with an actuation material 14 that accommodates acoustic stress wave-induced actuation stroke, the acoustic generator 12 is configured to deliver such a stress wave to the material. For clarity, this configuration is shown generally in FIG. 3A only schematically, with the acoustic stress wave generator configured as a normal-incidence generator, having a face of the generator in direct contact with an end face of the actuation material, but such is not a general requirement of the invention. If desired, a load 16 is supplied at the output of the actuation material. A stress wave reflector 18 shown in FIG. 3A is also not universally required but can be preferred, as explained above.

Figure 3B:
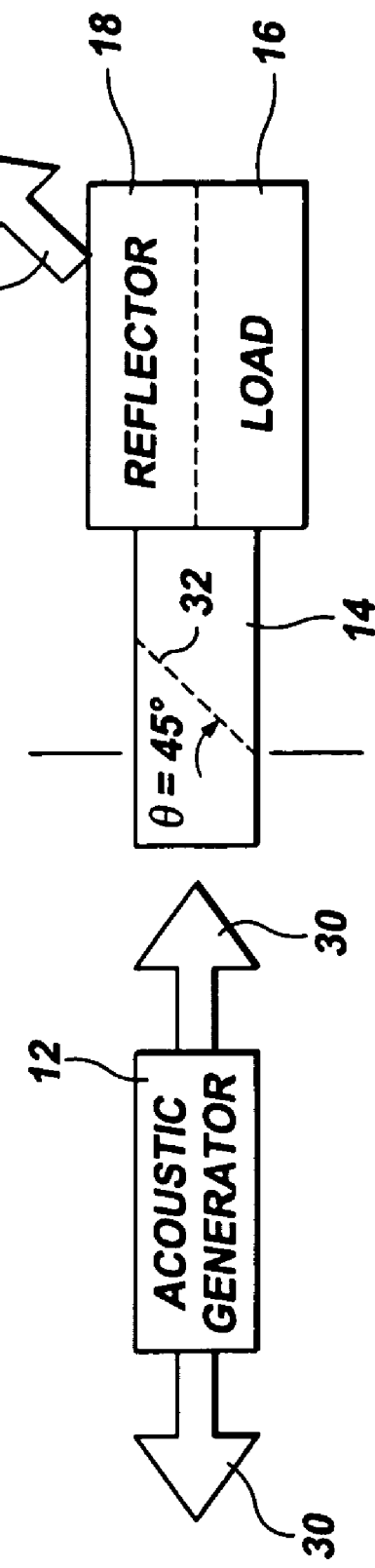

In accordance with the invention, an acoustic stress wave is generated to propagate through the actuation material in a direction selected to correspond to a desired actuation direction. Two examples of this actuation directionality control are shown schematically in FIGS. 3B-3D. In FIG. 3B, the acoustic generator 12 produces a longitudinal acoustic stress wave pulse 30 to be delivered to the actuation material 14. The longitudinal acoustic stress wave 30 here is tensile, having a maximum shear component at an angle of about 45° to the wave propagation direction. To produce this longitudinal stress wave, a 33-mode piezoelectric actuator can be mounted to an actuation material. Given a twinning actuation material, it is in this case preferred to orient the material such that the twin boundaries 32 of the material are also oriented at an angle of about 45° to the longitudinal wave propagation direction. This arrangement results in production of the largest possible shear strain along the twin boundaries as the longitudinal wave propagates through the material. With propagation of a longitudinal stress wave through the oriented actuation material, the tip of the actuation material, including a load 16 and/or reflector 18, then will produce a stroke 34 along the twin boundary orientation, e.g., the 45° angular orientation shown.

Referring to FIG. 3C, in a further example of acoustic actuation, the acoustic generator 12 is configured to produce a transverse acoustic stress wave 36 to be delivered to the actuation material 14. The transverse acoustic stress wave is here a shear wave in which the material motion is in a direction normal to the propagation direction, thereby having a maximum shear component at an angle of about 90° to the wave propagation direction. To obtain this transverse actuation, a 15-mode piezoelectric stack can be employed as the acoustic stress wave generator and can be mounted to an actuation material. For a twinning actuation material, it is in this case preferred to orient the material such that the twin boundaries 32 of the material are also oriented at an angle of about 90° to the transverse wave propagation direction. This arrangement results in production of the largest possible shear stress along the twin boundary 32 for the transverse wave. With propagation of a transverse stress wave through the oriented actuation material, the tip of the actuation material, including a load 16 and/or reflector 18 then will produce a stroke 36 along the twin boundary orientation, e.g., the 90° orientation shown.

FIG. 3D is a further example of an arrangement in which the acoustic generator 12 is configured to produce a transverse acoustic stress wave 36 to be delivered to the actuation material 14. Here the acoustic generator 12 is provided in an A-frame arrangement with two generators 41, 43 held by a frame structure 45. Each generator 41, 43 can be provided as, e.g., an active material such as the piezoelectric stack devices described above. The piezoelectric stacks are controlled relative to each other such that their extension and retraction cooperatively produce a single transverse acoustic stress wave 36.

As with the arrangement shown schematically in FIG. 3B, a transverse acoustic stress wave is here produced as a shear wave for which the material motion is in a direction normal to the propagation direction, thereby having a maximum shear component at an angle of about 90° to the wave propagation direction. Thus, as in the arrangement shown in FIG. 3B, here it can be preferred to orient the actuation material such that the twin boundaries 32 of the material are also oriented at an angle of about 90° to the transverse wave propagation direction. A stroke 47 along the twin boundary orientation will then be produced.

Figure 4A:
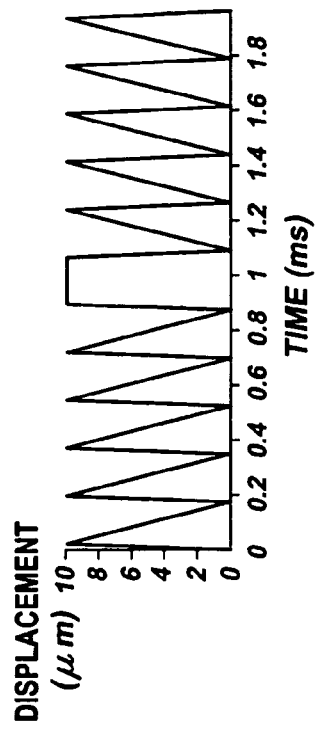
FIGS. 4A-4B are plots of six tensile displacement pulses of a piezoelectric acoustic stress wave generator and the resulting six actuation stroke extensions of a shape memory alloy actuation material, respectively.
Figure 4C:
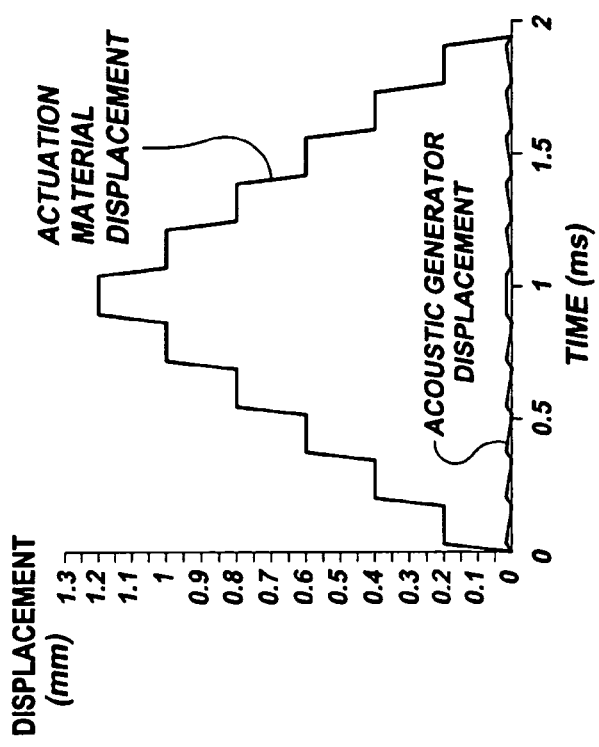
FIGS. 4C-4D are plots of six tensile displacement pulses and six compressive pulses of a piezoelectric acoustic stress wave generator and the resulting six actuation stroke extensions and six actuation stroke retractions of a shape memory alloy actuation material, respectively.
Figure 4B:
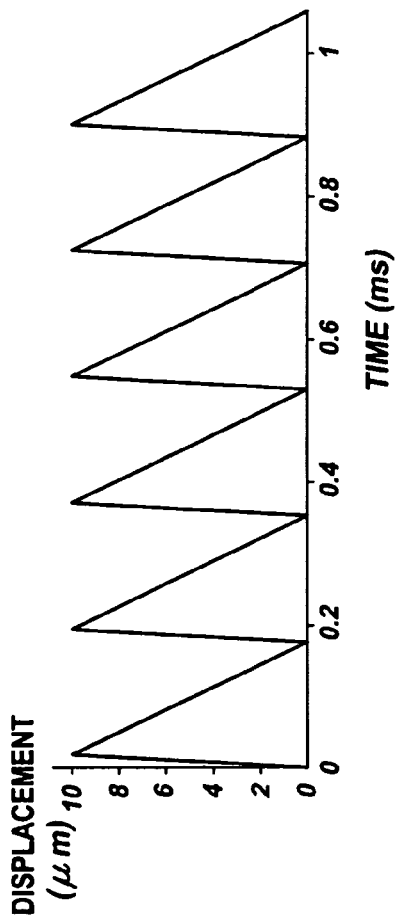

FIGS. 4A-4B are plots of the end displacement of a piezoelectric acoustic stress wave generation material and the resulting end displacement, or stroke, of a shape memory alloy actuation material, respectively, over the course of a sequence of acoustic stress waves, herein termed a train of acoustic stress pulses. The piezoelectric stack displacement for producing a train of tensile stress pulses is shown, with the resulting six extensions in actuation material. For each acoustic stress wave produced by a displacement of the piezoelectric stack, the shape memory alloy actuation material is extended beyond a current stroke position, and at the end of each stress wave, the actuation material maintains its position without power input. The train of tensile stress pulses produced by the plotted piezoelectric stack displacements thereby produces a ratcheting of actuation material stroke in a particularly efficient and effective manner. This example assumes that the shape memory material is of sufficient length that un-twinned material remains for actuation after each stress wave in the stress pulse sequence.

Figure 4D:
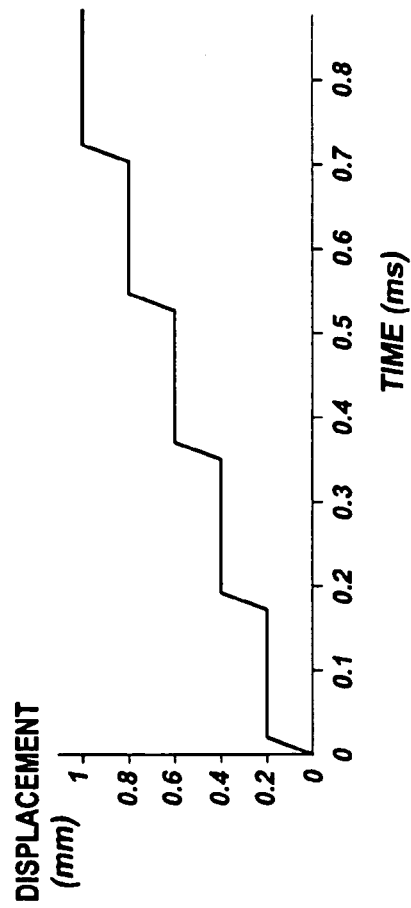

Note in the plots of FIGS. 4A-4B the difference in displacement scales between the piezoelectric material and the shape memory actuation material. This difference is highlighted in the plots of FIGS. 4C-4D. In FIG. 4C is plotted a sequence of piezoelectric material end displacements for producing a train of six tensile stress pulses followed by six compressive stress pulses. FIG. 4D plots the resulting stroke of a shape memory alloy actuation material. The sequence of stress pulses produced by the piezoelectric displacements is shown to result in multiplicative stroke extensions, followed by multiplicative stroke retractions back to the original actuation configuration.

Also plotted in FIG. 4D is the acoustic stress pulse generation sequence of FIG. 4C. This plotting of both the piezoelectric material extension and resulting the shape memory alloy extension on the same displacement scale indicates that it is possible to approximately define a stroke amplification factor for the acoustic actuator of the invention for the case where the actuation material is provided as a shape memory actuation material and the stress wave generation material is provided as an active material such as a piezoelectric material. The stroke amplification factor here relates the strain of the actuation material to the maximum strain of the stress wave generation material. It is to be noted that the amplification factor being defined here is not that of conventional, quasi-static actuators and instead relates to the ability of the shape memory material to hold a position without power input during a sequence of actuating pulses. A conventional stroke-amplified quasi-static actuator exhibits a strain and position that persists only as long as the actuator is energized. In contrast, in the acoustic actuator of the invention, the piezoelectric stress wave generation material operates cyclically, returning to its original dimensions at the end of each pulse, but the effect is an increasing, non-zero net strain on the actuation material, as evidenced by the ratcheting, multiplicative nature of stroke extension and retraction shown in the plots of FIG. 4.

To more quantitatively analyze this amplification factor, consider a Ni—Mn—Ga actuation crystal mounted on a longitudinal Lead Zirconate Titanate (PZT) stress wave generation material such that the Ni—Mn—Ga twin plane lies at 45° to the PZT material surface. Assume that the dimensions of the SMA and its material properties give it a much lower acoustic impedance than the PZT. In this case, the behavior of the PZT in response to a given voltage pulse will be close to its unstressed response, since most of the mechanical work produced by the PZT produces acoustic waves in the more compliant SMA, which can therefore only exert a small resulting force on the PZT. Thus, a linear increase in the applied stress wave generation voltage will produce an approximately linear rate of strain in the PZT, which results in an approximately constant velocity at the end of the PZT.

Based on Expression (2) given above, the stress is linearly related to the piezoelectric material velocity. In the current example, given that the PZT has a maximum strain of 10 µm when it is attached to the SMA, then a stress wave pulse voltage rise time of 20 µs will result in PZT end-face velocity of $-0.5 ms^{-1}$, where a negative velocity indicates the PZT is pulling on the SMA. This creates a tensile stress in the direction of stress wave propagation of about 8 MPa in the SMA, which exceeds the twinning threshold and persists as long as the pulse.

If it is assumed that a single mobile twin boundary exists in the SMA, and that the boundary moves at an average speed, $v_{twin} \approx 10\ ms^{-1}$ in response to propagation of the stress wave, then the total displacement stroke produced by each PZT pulse can be estimated as $d_{twin} = v_{twin} t_{pulse} \approx 200\ \mu m$. This is equivalent to a "stroke amplification" factor of about 20 per pulse. With subsequent pulses, as shown in the plots of FIG. 4, there is a multiplicative effect, due to the fact that the SMA actuation material holds its position after each pulse.

As a result, in this example, for each acoustic stress wave pulse, the SMA actuation material exhibits a net displacement that is about 20 times the displacement of the PZT acoustic stress wave generator displacement, and the total SMA displacement is multiplied by the number of stress waves in a train of stress pulses. Thus, for the 6-pulse sequence of FIGS. 4A-4B, a total amplification factor of 120 is achieved between the PZT acoustic stress wave generator displacement and the SMA actuation material displacement. This stroke amplification is a particularly important feature of the acoustic actuator of the invention and enables its application to a range of engineering problems for which the amplification, as well as compact design and high output strain, are beneficial.

For the acoustic stress wave pulses generated by the piezoelectric stack displacements shown in the plots of FIG. 4, if the total duration of a pulse is considered, the integral of the instantaneous momentum imparted to the actuation material from the acoustic stress wave generator must be zero. Actuation is thus achieved by maximizing the magnitude of the stress that is of the desired sign at the expense of the pulse duration. The design of an actuation controller (20 in FIG. 1) preferably enables this condition. Assuming a piezoelectric stress wave generation material, then this condition imposes a requirement for an actuation controller that can effectively drive a large electrical current into or out of the piezoelectric material in the short rise time of the pulse and maintain a much smaller reverse, i.e., unwanted, current over the remaining duration of the pulse. In analogy to the mechanical output, if the instantaneous current into the acoustic stress wave generation material is integrated over the duration of the pulse, the result must be zero if net polarization of the material does not occur.

In one example actuation controller provided by the invention for a piezoelectric acoustic stress wave generation material, driver circuits are implemented with voltage-mode devices that operate to control the voltage, rather than the current, across a piezoelectric material. Such voltage-mode devices have the advantage of linear operation at high frequencies. Whatever control circuit implementation is employed, it is preferred that such enables a close matching of impedances of the driver circuit and cables with that of the piezoelectric material. Because the mechanical displacement of the piezoelectric material that results from each control volt to the piezoelectric material is inversely proportional to the total circuit capacitance, the total capacitance should be minimized.

Figure 5:
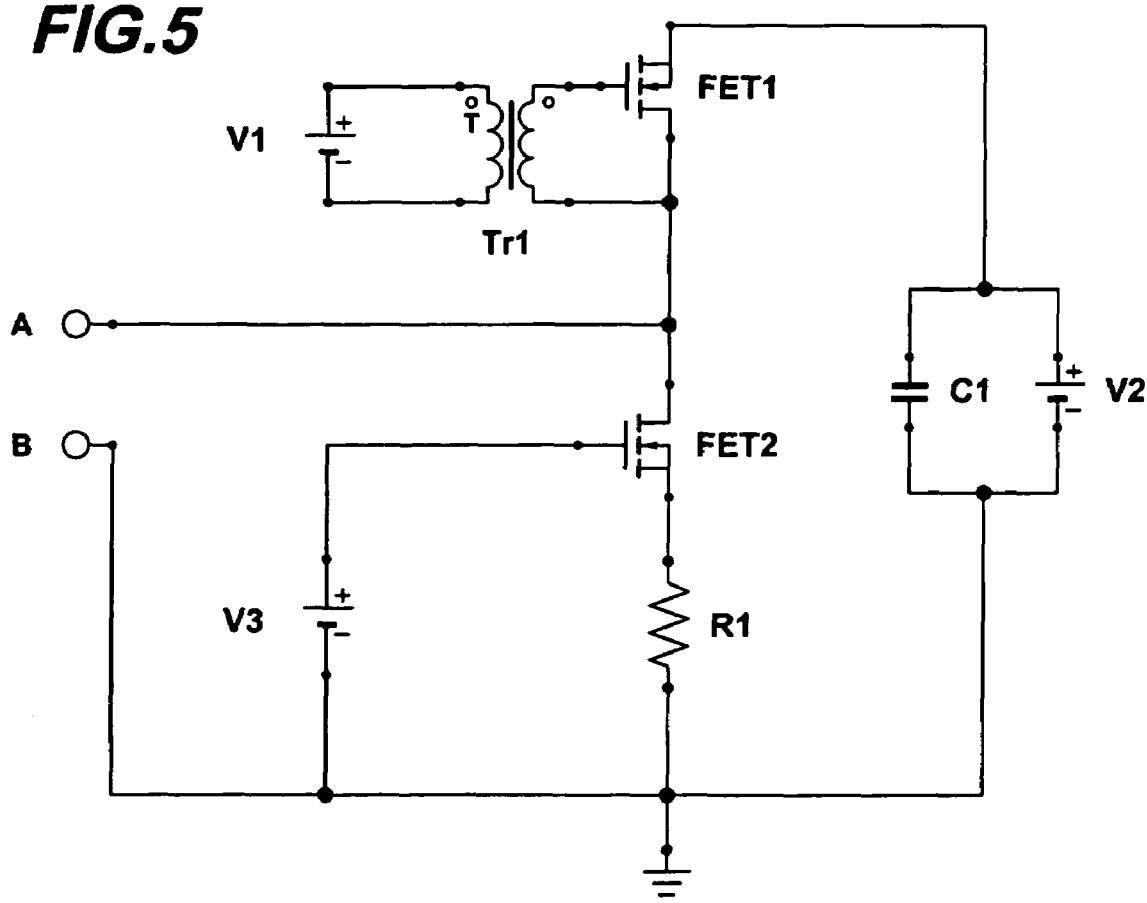
FIG. 5 is a circuit diagram of an example acoustic actuator controller provided by the invention.

FIG. 5 is a circuit diagram of an example actuation control circuit 60. The values of the components included in the circuit will depend largely on the specific acoustic stress wave generation material being employed as well as the mode of operation of the acoustic actuator. The operation of the circuit can be summarized as follows. A triggering signal V1 is provided to the circuit. A transformer Tr1 provides isolation between the triggering signal input and the rest of the circuit, which operates at a high voltage. When the triggering signal from the transformer to the gate of the FET1 exceeds a threshold voltage, the field-effect transistor FET1 is turned on, and current can flow from voltage source V2 through the FET1 to the terminal A to deliver the voltage to the stress wave generation material. Terminal A can be connected to the positive lead of the stress wave generation material, with terminal B connected to the negative lead of the material for delivery of the voltage. The bypass capacitor C1 is placed in parallel with the voltage supply V2 to improve the high frequency response of the supply, allowing a high current flow during the rapid change in the piezoelectric stack voltage. A constant voltage V3 is supplied to the gate of field effect transistor FET2, which results in a nearly constant current through the field effect transistor and R1, in order to discharge the piezoelectric stack at a fixed, slower rate. This circuit configuration enables production of a voltage signal with a fast rise time and slow decay, for compressive acoustic stress wave generation. In the conventional manner, the circuit can be modified to alternatively generate a voltage signal resulting in tensile acoustic stress wave generation, or to generate voltage signals for both compressive and tensile acoustic stress wave generation.

EXAMPLE 1

Figure 6:
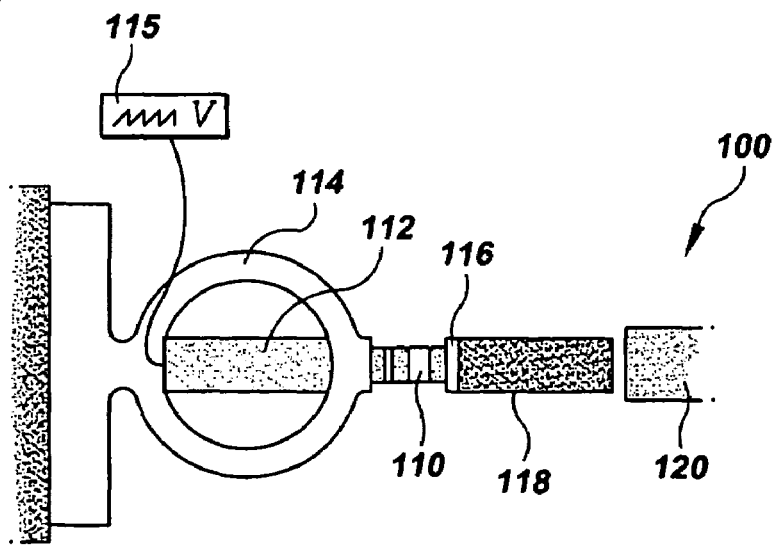
FIG. 6 is a schematic diagram of an experimental acoustic actuator built in accordance with the invention.

An acoustic actuator in accordance with the invention was built for experimental analysis of the actuator performance. A schematic view of the experimental actuator 100 is shown in FIG. 6. The actuation material was provided as a single crystal FSMA 110, specifically, a single crystal of tetragonal Ni—Mn—Ga measuring 6.58 mm in a longitudinal actuation direction, with a cross section of 2.35 mm×3.87 mm. The crystal was heat treated and cooled under stress, in the manner described above, to obtain a single twin variant structure prior to actuation.

The acoustic generator was provided as a piezoelectric stack 112, specifically, a Piezo Systems T18-H5-104 piezoelectric stack actuator, which is capable of producing about 14 μm of displacement at an input actuation voltage of about 100 V. A clamp 114 was employed to hold the stack in place and position the stack relative to the other acoustic actuator elements, without the use of a bonding agent. The clamp was also employed, in the manner described previously, for applying a pre-stress on the piezoelectric stack, to improve the acoustic generation performance in the manner described above. An epoxy, Loctite E-120HP, was used to join the FSMA 110 to the clamp 114. The piezoelectric stack was connected to a control circuit 115, represented schematically in the figure, to apply acoustic generation voltage control signals to the stack in the manner described above in connection with the circuit of FIG. 5.

At the right end of the actuation material was provided a single layer of PZT 116 to be employed as a stress sensor to measure transient acoustic stress waves propagating through the extent of the FSMA actuation material 110 and reaching the right end of the FSMA material. A brass reflector 118 was in turn attached to the PZT 116 to prevent propagation of an inverted stress wave through the actuation material 110. The reflector was provided as a rectangular prism, having a cross section of 8.3 mm×5.8 mm on the face bonded to the FSMA crystal, and a length of 9.6 mm. This reflector size was selected to disperse the stress wave before being reflected off of the free end of the reflector to return to the FSMA. A short distance from the end of the brass reflector was positioned an ADE 3800 capacitive position sensor 120 to capture an accurate measurement of the displacement, or stroke, of the end of the actuation material 110.

To analyze the FSMA acoustic actuation, the FSMA crystal was first extended and then when configured in the acoustic actuator was compressed step-wise by a series of acoustic stress waves generated by the piezoelectric stack. The initial extension was accomplished by placing a transverse magnetic field of about 4 kG across the crystal, and then removing the field before actuation in the acoustic actuator. Actuation was started with several individual compressive acoustic waves that were applied via manual operation of the piezoelectric stack. Then electrical control of the piezoelectric stack was carried out in the manner explained previously.

Figure 7A:
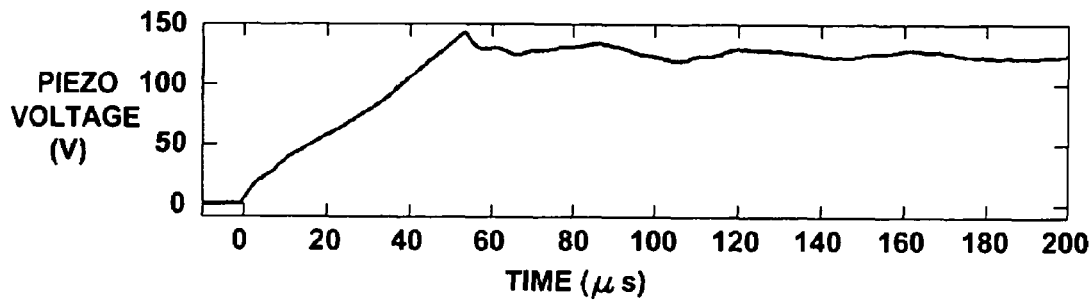
FIGS. 7A-7B are plots of an experimental acoustic stress wave pulse and the resulting strain measured in an actuation material in the configuration of FIG. 6, respectively.

FIG. 7A is a plot of the voltage control pulse applied to the piezoelectric stack for producing an acoustic stress wave. The voltage control pulse was a saw-tooth pulse rising from 0 V quickly to 150 V and then slowly returning to 0 V; the microsecond scale of the plot of FIG. 7A does not allow for inclusion of the full 100 ms extent of the voltage control pulse fall time. The fast voltage pulse rise caused the piezoelectric stack to expand quickly, in about 60 μs, and generate a compressive stress wave having a magnitude greater than the required actuation stress, i.e., the resulting stress wave peak stress was greater than the twinning stress in the crystal, thereby enabling stroke of the FSMA actuation material.

Figure 7B:
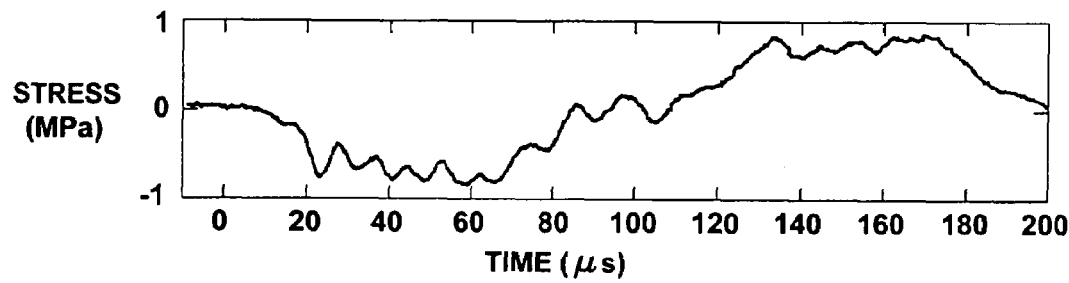

FIG. 7B is a plot of the measured propagated stress wave in the FSMA actuation material resulting from the control voltage pulse plotted in FIG. 7A. It is found that this stress wave is not ideal, reaching nearly the same tensile stress as compressive stress. The oscillations along the peak of the stress wave are due to the length of the input control pulse relative to the period of the resonance of the piezoelectric stack. In 50 μs, a sound wave can travel from one end of the stack to the other approximately 7 times, based on the speed of sound calculated from stack properties, resulting in the 7 small peaks along the major peak of the wave.

Figure 8A:
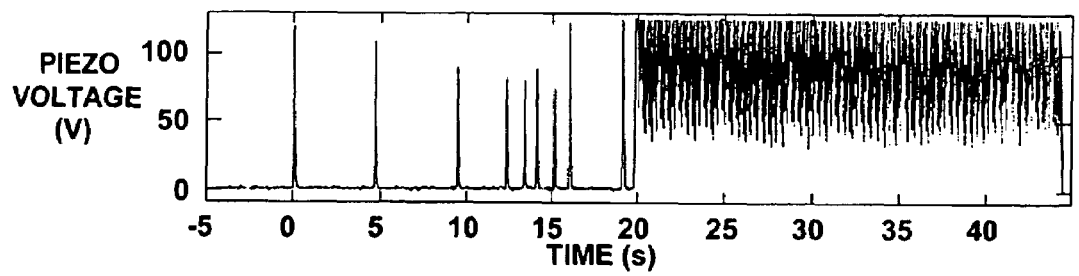
FIGS. 8A-8B are plots of a sequence of experimental acoustic stress wave pulses and the resulting strain measured in an actuation material in the experimental acoustic actuator of FIG. 6, respectively.
Figure 8B:
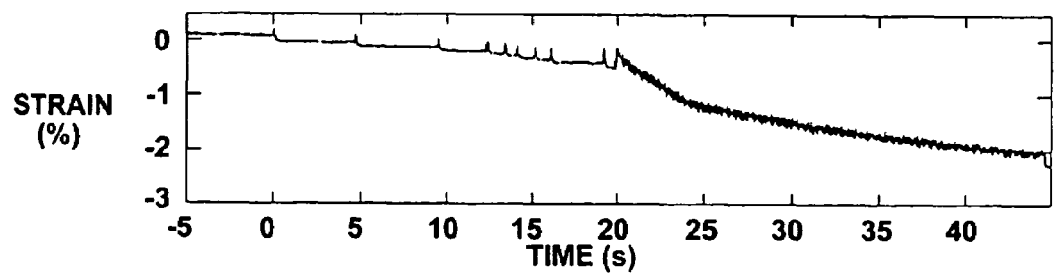

FIGS. 8A-8B are plots of the actuation results for this piezoelectric voltage control pulse and resulting stress wave over a sequence of such pulses. After several manually applied actuation material compression strokes, the control circuit was run at about 7.5 Hz for several seconds, with significant actuation of the actuation material continuing. FIG. 8A plots the control voltage pulses for generating the piezoelectric stack-based stress waves, and FIG. 8B plots the resulting strain in the FSMA actuation material for compressing the material in a step-wise, inch-worm type actuation sequence. Twin boundary motion induced by the stress wave was apparent as the steady state position of the free end of the FSMA was different before and after each pulse. Despite the less than ideal stress wave shape, the asymmetry in the stress wave was sufficient to effect significant strain in the FSMA crystal.

EXAMPLE 2

Figure 9:
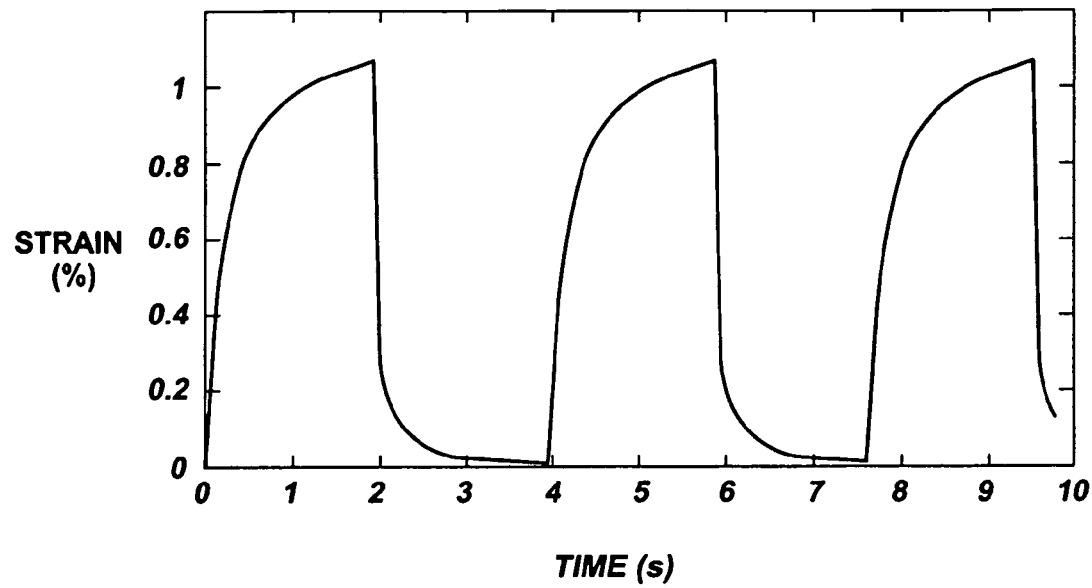
FIG. 9 is a plot of measured strain in the actuation material in the experimental acoustic actuator of FIG. 6, over a sequence of applied acoustic stress pulses.

The acoustic actuator of Example 1 was configured for bidirectional actuation without a load to produce both extensional stroke as well as compression under a no-load condition. To achieve this operation, the pre-stress applied by the piezoelectric stack clamp 114 was increased and the rise time of the input control voltage pulse was decreased. The input control voltage magnitude for controlling the piezoelectric stack was 100 V and the pulse repetition rate was set at 100 Hz. FIG. 9 is a plot of the resulting strain measured in the FSMA actuation material. The extensional actuation was slightly less effective than the compressive actuation. This is evident in FIG. 9, where the time required to extend the FSMA crystal (increasing strain) is somewhat longer than the time required to compress the crystal (decreasing strain). This asymmetry in response time may be due to insufficient piezoelectric stack pre-stress.

EXAMPLE 3

Figure 10:
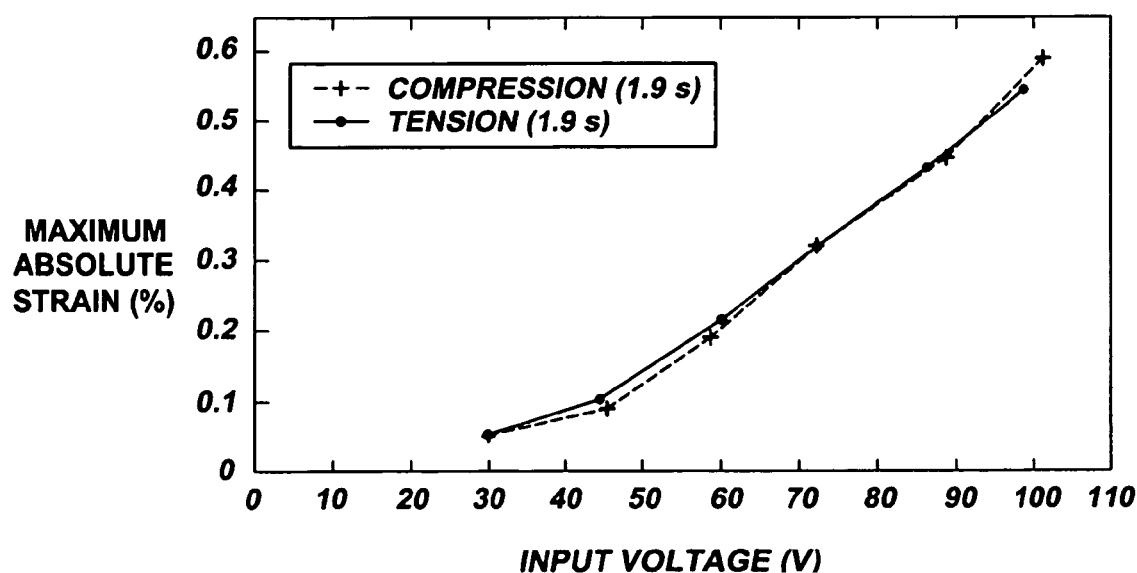
FIG. 10 is a plot of the measured maximum absolute strain generated in the actuation material of the experimental actuator of FIG. 6, after 1.9 s for each selected voltage of the plot.

The acoustic actuator of Example 1 was configured for bidirectional actuation without a load and for a range of piezoelectric stack control voltage pulses. The acoustic actuator was operated for 1.9 s, corresponding to 190 piezoelectric stack displacements and corresponding acoustic stress waves, for each selected voltage. The input voltage was varied linearly between 20 V and 100 V. The pulse repetition rate was 100 Hz. FIG. 10 is a plot of the maximum absolute strain generated in the FSMA actuation material after 1.9 s for each selected voltage. The absolute value of strain is shown to enable comparison between tension and compression.

It was found that an increase in the input voltage indirectly increased the actuation strain achieved by each pulse, by generating larger stress waves with the piezoelectric stack. The stress waves show a nearly linear relationship between the input voltage and the amplitude of the generated stress wave. A linear relationship between the stress wave amplitude and the strain achieved in the actuation material by a stress wave is not entirely expected. Incident stress waves with increasingly higher amplitude cause reflected, inverted stress waves of correspondingly increased amplitude that could potentially impede or reverse actuation. This type of reflected inverted stress wave actuation did not affect the bi-directional actuation observed here, however.

One explanation for the observed increase in maximum absolute strain with increasing input voltage is that various portions of the FSMA crystal may have slightly different properties, and in particular the stress required to move twin boundaries may vary along the crystal. An increase in the input voltage results in a stress wave having a stress magnitude that is sufficiently large to exceed the required twinning stress over most of the FSMA crystal.

EXAMPLE 4

Figure 11:
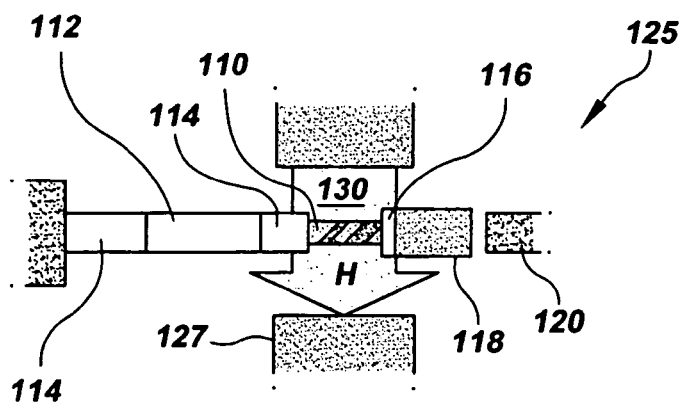
FIG. 11 is a schematic diagram of an experimental magneto-acoustic actuator built in accordance with the invention.

The acoustic actuator of Example 1 was configured for step-wise compressive actuation from an acoustic stress wave augmented by a magnetic field. FIG. 11 is a schematic view of the resulting magneto-acoustic actuator. The FSMA actuation material 110 of Example 1 was arranged with the piezoelectric stack 112, clamp 114, reflector 118, and capacitive displacement sensor 120 of FIG. 1. An electromagnet 127 capable of generating a 4 kG magnetic field 130 was placed around the actuation material as shown with the material oriented such that the twin boundaries were 45° with the longitudinal stroke. With this arrangement, the resulting magnetic field was transverse to the length of the actuation material.

In testing, the magnetic field strength was ramped linearly up and down while a train of compressive acoustic stress pulses was continuously applied to the actuation material. A pulse repetition rate of 100 Hz was employed. Before each magneto-acoustic actuation measurement was made, the actuation crystal was manually compressed so that the crystal began to actuate as a single twin variant. A variety of magnetic field levels, field ramp rates, and acoustic stress pulse amplitudes were employed.

Figure 12:
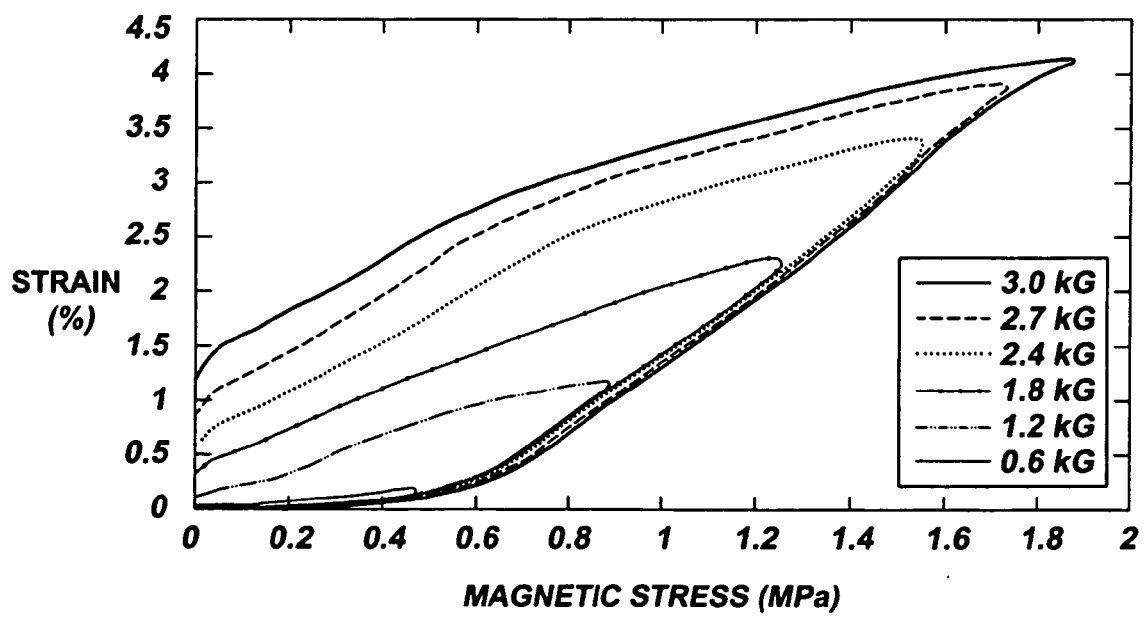
FIG. 12 is a plot of measured strain induced in the actuation material employed in the magneto-acoustic actuator of FIG. 11 as a function of ramping magnetic field stress for six different magnetic field strengths indicated in the plot.

FIG. 12 is a plot of strain induced in the actuation material as a function of ramping magnetic field stress for six different magnetic field strengths. The measured magnetic field was converted to an equivalent magnetic stress so that it could be easily compared with an applied mechanical stress. The magneto-acoustic operation exhibited several characteristics. First, the compressive acoustic pulses were found to act as a restoring force as the magnetic field was decreased. Additionally, the acoustic pulses enabled an increasing magnetic field to accomplish more twin boundary motion at lower fields. For instance, with the input control voltage set at 100 V, the magneto-acoustic actuator reaches 1% strain as the magnetic stress rises to about 0.85 MPa. With the input voltage at 40 V, the actuation material does not reach 1% strain until the magnetic stress is increased to about 1.3 MPa.

EXAMPLE 5

Figure 13:
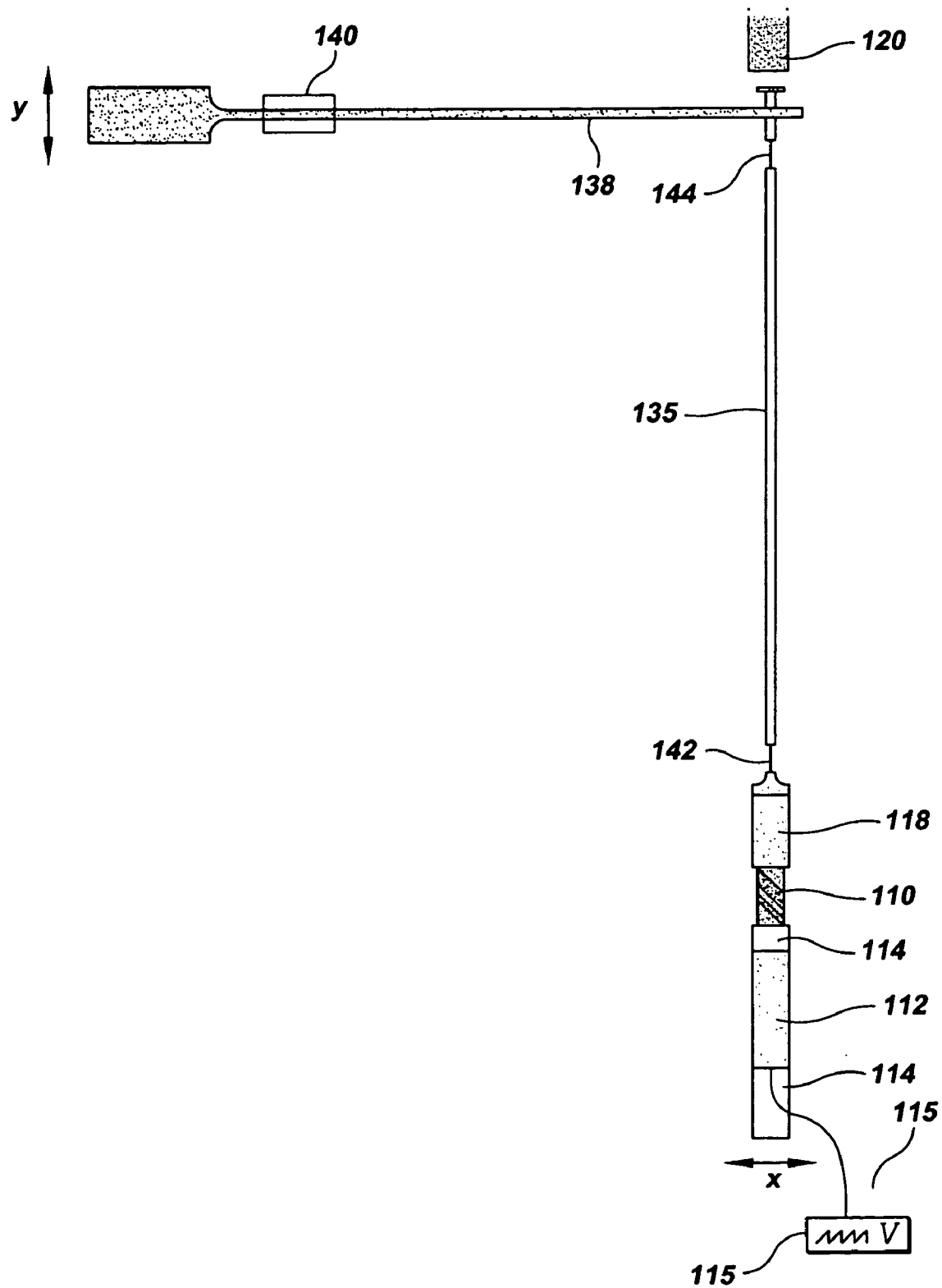
FIG. 13 is a schematic diagram of an experimental acoustic actuator built in accordance with the invention including an applied load.

The acoustic actuator of Example 1 was configured with a spring-load testing device to analyze output work capabilities of the acoustic actuator. FIG. 13 is a schematic side view of the spring-loaded actuator arrangement. Here the FSMA actuation material 110 employed had a length of 10 mm when compressed and a cross section of about 3.9 mm×3.9 mm. The clamp 114 of the piezoelectric stack 112 was mounted directly to the FSMA actuation material 110 by the adhesive DP-810 from 3M. All other bonds were made using Loctite 480.

In the arrangement, a pushrod 135 was positioned at the output of the stress wave reflector 118, with the capacitive displacement sensor 120 then located at the end of the pushrod. A load flexure 138 was positioned on the end of the pushrod. A pair of strain gauges 140 was mounted on the sides of the spring load flexure 138. The stiffness and force of the flexure was calibrated using a set of precision gram weights and an ADE 3800 position sensor.

This arrangement was selected to apply a longitudinal stress wave to the FSMA actuation material while minimizing transverse stresses and moments on the material. The spring flexure being acted against provided both a load and, with the strain gauges, a means of accurately measuring the force on the actuator. The length of the spring flexure was selected to ensure that the flexure behaved linearly over the entire stroke displacement range of the acoustic actuator. The pushrod 135 was configured with two small flexures 142, 144 that allowed the rod to bend while transmitting the spring load to the actuation material. This pushrod flexibility allows the reflector 118 at the end of the actuation material to travel along a diagonal stroke path, in the manner depicted in FIG. 3B, without experiencing significant transverse forces.

The piezoelectric stack clamp 114 was mounted to micrometer stages to allow for positioning of the actuator so that the pushrod would be as straight as possible at the start of actuation. The micrometer stages also were used to move the mount for the spring flexure along the direction of actuation and to control the application of a pre-stress to the entire actuator. This actuator pre-stress is much smaller than the pre-stress applied to the piezoelectric stack by the clamp 114.

Actuation with a selected flexure load in place began at zero strain and a selected pre-stress level. The input peak-to-peak control voltage was increased over the range of 0 V to 100 V. To retract the actuator, compressive pulses were employed, with the control voltage waveform increased rapidly from 0 V to a specified voltage up to 100 V, and then decreased slowly back to 0 V. To extend the actuator, tensile pulses were employed, with the control voltage waveform reduced rapidly from a specified positive voltage down to 0 V, and then increased slowly back to the specified voltage.

At each selected input voltage, acoustic actuation was continued until a steady state of actuation was reached. The time required to reach this steady state varied from 10 s to 60 s. Once steady state was reached, the strain in the material was measured and then the input control voltage was increased. After the peak tensile input voltage of 100 V was reached, the voltage was reduced and the polarity switched from tensile to compressive. The amplitude of the input voltage was then increased in the same manner up to a magnitude of 100 V. In operation, tensile stress waves elongated the actuation material and reduced the tensile stress or increased the compressive stress.

Figure 14A:
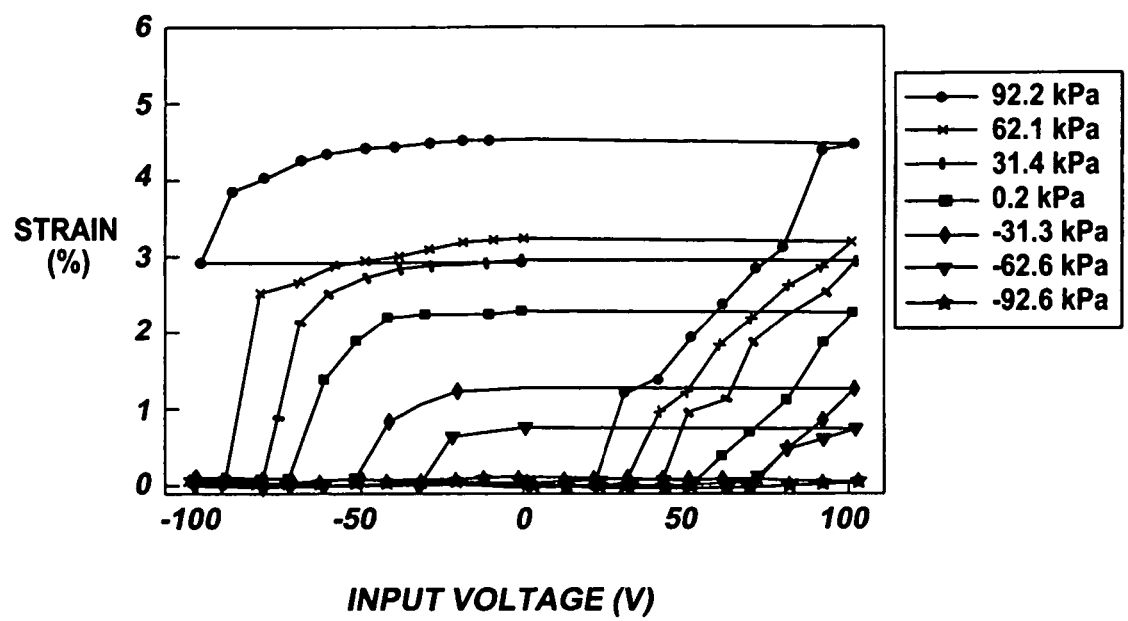
FIG. 14A is a plot of the actuation strain measured in the actuation material for the experimental acoustic actuator of FIG. 13, as a function of input control voltage for the range of actuator pre-stresses shown in the legend, measured before the start of actuation, with a load flexure having an equivalent stiffness of 1.21 MPa per unit area of actuation material.
Figure 14B:
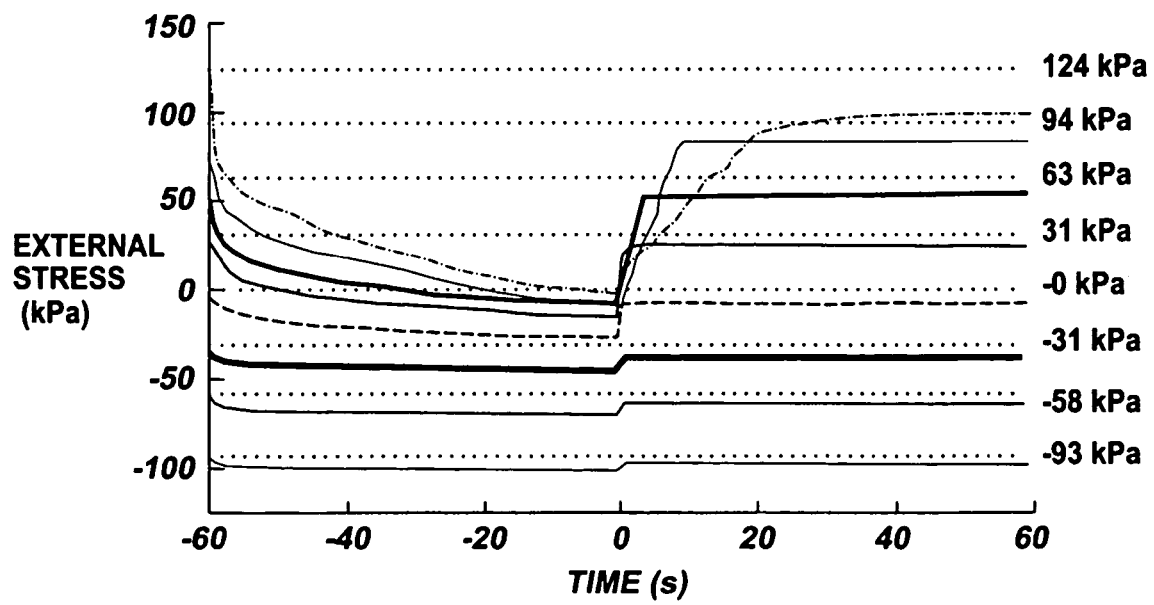
FIG. 14B is a plot of measured actuator stress as a function of time for the experimental acoustic actuator of FIG. 13 including a load flexure having an equivalent stiffness of 4.78 MPa per unit area of actuation material.

FIG. 14A is a plot of the actuation strain in the actuation material as a function of input control voltage for the range of actuator pre-stresses shown in the legend, measured before the start of actuation, with a flexure having a stiffness equivalent to 1.21 MPa per unit area of FSMA material. FIG. 14B is a plot of actuator stress as a function of time for a flexure having an equivalent stiffness of 4.78 MPa. In both FIG. 14A and FIG. 14B, negative-polarity control voltage values correspond to compressive stress waves, with the positive-polarity voltage values corresponding to extensional stress waves. The actuator pre-stress is indicated on the right-hand axis, and was measured before the start of actuation. Each actuation cycle represented in FIG. 14B was begun with a fully compressed actuation material. The input control voltage was 100 V and the pulse repetition rate was 50 Hz. The compressive pre-stress limit was determined by the point at which visible actuation no longer occurred. The tensile pre-stress limit was determined by predictive bond failure analysis.

With these examples, it is demonstrated that the acoustic actuator of the invention, when incorporating a twinning actuation material such as a FSMA, exhibits the unique ability of being able to actuate to a selected stroke position by a stress wave and remain in that position until a reverse actuation stress wave pulse is applied. When in an actuated stroke position, low or no power is required to maintain the position. A high output strain is produced by the actuator, and no moving parts are required when an active material such as a piezoelectric stack is employed as an acoustic generator. The acoustic actuator of the invention is therefore well-suited for micropositioning applications.

Thus, it is shown that the invention provides an acoustic actuator with a range of superior characteristics, including large actuation stroke, fast actuation response time, no significant thermal constraints, and conveniently small size. These qualities are achieved through the discovery that actuation materials, including those conventionally actuated by, e.g., electric field, magnetic field, and/or temperature field, can instead be actuated by an acoustic stress wave. It is recognized, of course, that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. An acoustic actuator comprising:
   an acoustic stress wave generator that generates asymmetric acoustic stress waves; and
   an actuation material operatively positioned relative to the acoustic stress wave generator for delivery of asymmetric acoustic stress waves from the generator to the actuation material.

2. The acoustic actuator of claim 1 further comprising an actuation control circuit connected to control generation of acoustic stress waves.

3. The acoustic actuator of claim 1 wherein the actuation material comprises an output end that is positioned for effecting an actuation stroke in response to an acoustic stress wave.

4. The acoustic actuator of claim 1 further comprising a mechanical reflector operatively positioned at an output end of the actuation material to reflect acoustic stress wave pulses reaching the output end of the actuation material.

5. The acoustic actuator of claim 1 further comprising a mechanical load positioned at an output end of the actuation material.

6. The acoustic actuator of claim 1 wherein the acoustic stress wave generator comprises an acoustic stress wave generator material.

7. The acoustic actuator of claim 6 wherein the acoustic stress wave generator material is characterized by a generator material acoustic impedance that is greater than a characteristic acoustic impedance of the actuation material.

8. The acoustic actuator of claim 6 wherein an output end of the acoustic stress wave generator material is mounted to an input face of the actuation material.

9. The acoustic actuator of claim 8 wherein the output end of the acoustic stress wave generator material is coupled to the input face of the actuation material for direct transmission of acoustic stress waves from the generator material to the actuation material.

10. The acoustic actuator of claim 6 wherein the acoustic stress wave generator material is characterized by a mechanical stroke output that generates an acoustic stress wave.

11. The acoustic actuator of claim 1 wherein the actuation material is characterized by two or more stable mechanical states.

12. The acoustic actuator of claim 1 wherein the actuation material is characterized by a lattice structure that supports propagation of acoustic stress waves through the material.

13. The acoustic actuator of claim 1 wherein the actuation material is a single crystal material.

14. The acoustic actuator of claim 1 wherein the actuation material is a polycrystalline material.

15. The acoustic actuator of claim 3 wherein the output end of the actuation material that is positioned for effecting an actuation stroke is characterized by a stroke position that is maintained without energy input.

16. The acoustic actuator of claim 1 wherein the actuation material comprises an active material operatively positioned relative to the acoustic stress wave generator to actuate in response to the acoustic stress waves without other actuation stimulus.

17. The acoustic actuator of claim 16 wherein the actuation material comprises a magnetic field-based active material operatively positioned relative to the acoustic stress wave generator to actuate in response to the acoustic stress waves without magnetic field stimulus.

18. The acoustic actuator of claim 16 wherein the actuation material a comprises a thermal field-based active material operatively positioned relative to the acoustic stress wave generator to actuate in response to the acoustic stress waves without thermal stimulus.

19. The acoustic actuator of claim 1 wherein the actuation material a is operatively positioned relative to the acoustic stress wave generator for the acoustic stress waves to deform the actuation material by reorienting a selected one or more crystallographic states of the actuation material as the acoustic stress waves propagate through the actuation material.

20. The acoustic actuator of claim 1 wherein the acoustic wave generator and the actuation material each comprise an active material and elements of the acoustic actuator are configured such that substantially all actuator motion consists of active material deformation.

21. The acoustic actuator of claim 1 wherein the actuation material is characterized by two or more stable crystallographic twin variants.

22. The acoustic actuator of claim 21 wherein the actuation material comprises a shape memory alloy.

23. The acoustic actuator of claim 22 wherein the shape memory alloy comprises a crystallographic structure that accommodates reversible deformation between a low-temperature martensitic material phase and a high-temperature austenitic material phase.

24. The acoustic actuator of claim 22 wherein the shape memory alloy comprises a ferromagnetic shape memory alloy.

25. The acoustic actuator of claim 24 wherein the ferromagnetic shape memory alloy comprises a Ni—Mn—Ga alloy.

26. The acoustic actuator of claim 25 wherein the Ni—Mn—Ga alloy comprises $Ni_xMn_{1.16-1.75x}Ga_{0.75x-0.16}$, where x is between about 0.46 and about 0.52.

27. The acoustic actuator of claim 1 wherein the acoustic stress wave generator comprises a mechanical assembly including at least one moving element.

28. The acoustic actuator of claim 1 wherein the acoustic stress wave generator comprises an electric field-based active material.

29. The acoustic actuator of claim 1 wherein the acoustic stress wave generator comprises a magnetic fieldbased active material.

30. The acoustic actuator of claim 29 wherein the magnetic field-based active material comprises a magnetostrictive material.

31. The acoustic actuator of claim 30 wherein the magnetostrictive material comprises $Tb_{0.3}Dy_{0.7}Fe_2$.

32. The acoustic actuator of claim 28 wherein the electric field-based active material comprises a piezoelectric material.

33. The acoustic actuator of claim 32 wherein the piezoelectric material comprises lead zirconate titanate.

34. The acoustic actuator of claim 32 wherein the piezoelectric material comprises a 33-mode piezoelectric material configured for generating a longitudinal acoustic stress wave.

35. The acoustic actuator of claim 32 wherein the piezoelectric material comprises a 15-mode piezoelectric material configured for generating a transverse acoustic stress wave.

36. The acoustic actuator of claim 32 wherein the piezoelectric material comprises a plurality of 33-mode piezoelectric materials each configured with an axis oriented at an angle of about 45° C. to a longitudinal axis of the actuation material and connected to cooperatively generate the transverse acoustic stress wave.

37. The acoustic actuator of claim 34 wherein the actuation material is characterized by two or more stable crystallographic twin variants and is oriented relative to the piezoelectric material with a direction normal to a twin boundary, between the twin variants, at an angle of approximately 45 degrees with a direction of propagation of the longitudinal stress wave.

38. The acoustic actuator of claim 35 wherein the actuation material is characterized by two or more stable crystallographic twin variants and is oriented relative to the piezoelectric material with a direction normal to a twin boundary, between the twin variants, being parallel to a direction of propagation of the transverse stress wave.

39. The acoustic actuator of claim 32 wherein the piezoelectric material comprises a single-layer of piezoelectric material.

40. The acoustic actuator of claim 32 wherein the piezoelectric material comprises a stack of piezoelectric material layers.

41. The acoustic actuator of claim 40 further comprising a mechanical clamp applied to the piezoelectric material layer stack to impose a compressive mechanical pre-stress on the stack.

42. The acoustic actuator of claim 1 wherein the asymmetric stress wave is characterized by a peak stress magnitude that is greater than a threshold actuation stress characteristic of the actuation material.

43. The acoustic actuator of claim 42 wherein the asymmetric stress wave is characterized by a peak compressive stress magnitude that is greater than a threshold actuation stress for compression of the actuation material, and is characterized by a tensile stress magnitude that is less than a threshold actuation stress for extension of the actuation material.

44. The acoustic actuator of claim 42 wherein the asymmetric stress wave is characterized by a peak tensile stress magnitude that is greater than a threshold actuation stress for extension of the actuation material, and is characterized by a compressive stress magnitude that is less than a threshold actuation stress for compression of the actuation material.

45. The acoustic actuator of claim 42 wherein the actuation material is characterized by two or more crystallographic twin variants and a peak shear stress magnitude of the acoustic stress wave along a twin boundary between the twin variants is greater than a twinning stress characteristic of the actuation material.

46. The acoustic actuator of claim 1 further comprising an actuation controller configured to deliver a voltage control pulse to the acoustic stress wave generator for producing the asymmetric stress wave.

* * * * *